US007678933B2

(12) United States Patent
Lee et al.

(10) Patent No.: US 7,678,933 B2
(45) Date of Patent: Mar. 16, 2010

(54) TRANSITION METAL COMPLEXES AND PREPARATION METHODS THEREOF

(75) Inventors: Choong-Hoon Lee, Daejeon Metropolitan (KR); Eun-Jung Lee, Daejeon Metropolitan (KR); Seung-Whan Jung, Suwon-Si (KR); Jung-A Lee, Gangwon-Do (KR); Bo-Ram Lee, Seoul (KR); Bun-Yeoul Lee, Suwon-Si (KR)

(73) Assignee: LG Chem, Ltd. (KR)

( * ) Notice: Subject to any disclaimer, the term of this patent is extended or adjusted under 35 U.S.C. 154(b) by 41 days.

(21) Appl. No.: 12/087,215

(22) PCT Filed: Dec. 29, 2006

(86) PCT No.: PCT/KR2006/005908

§ 371 (c)(1),
(2), (4) Date: Jun. 25, 2008

(87) PCT Pub. No.: WO2007/078134

PCT Pub. Date: Jul. 12, 2007

(65) Prior Publication Data

US 2009/0030221 A1 Jan. 29, 2009

(30) Foreign Application Priority Data

Dec. 30, 2005 (KR) ...................... 10-2005-0135900
Jul. 18, 2006 (KR) ...................... 10-2006-0067117

(51) Int. Cl.
*C07F 7/00* (2006.01)
*C07C 211/00* (2006.01)
*C07C 49/00* (2006.01)

(52) U.S. Cl. ............................... 556/19; 556/2; 556/52; 564/336; 568/330; 568/332; 568/379; 568/380

(58) Field of Classification Search ................... 556/19, 556/20, 52; 564/336; 568/330, 332, 379, 568/380
See application file for complete search history.

(56) References Cited

U.S. PATENT DOCUMENTS

| | | | | |
|---|---|---|---|---|
| 5,064,802 | A | 11/1991 | Stevens et al. | |
| 6,153,776 | A | 11/2000 | Patton et al. | |
| 6,548,686 | B2 | 4/2003 | Nboka et al. | |
| 6,617,466 | B1 | 9/2003 | Canich | |
| 6,636,597 | B2 | 10/2003 | Porter et al. | |
| 6,686,488 | B2 | 2/2004 | Wilson et al. | |
| 6,825,369 | B1 | 11/2004 | Stevens et al. | |
| 7,517,940 | B2 * | 4/2009 | Lee et al. .................... | 526/160 |

FOREIGN PATENT DOCUMENTS

| | | | |
|---|---|---|---|
| EP | 0 311 899 | A2 * | 4/1989 |
| JP | 8-325283 | A | 12/1996 |

OTHER PUBLICATIONS

Cho et al., "o-Phenylene-Bridged Cp/Amino Titanium Complexes for Ethylene/1-Hexene Copolymerizations", Organometallics, vol. 25, No. 9, pp. 2133-2134, 2006.
Gibson et al., "Advances in Non-Metallocene Olefin Polymerization Catalysis", Chem. Rev. vol. 103, pp. 283-315, 2003.
Chen et al., "A Novel Phenolate "Constrained Geometry" Catalyst System. Efficient Synthesis, Structural Characterization, and α-Olefin Polymerization Catalysis", Organometallics, vol. 16, pp. 5958-5963, 1997.
Zhang et al., "Constrained Geometry Tetramethylcyclopentadienly-phenoxytitanium Dichlorides: Template Synthesis, Structures, and Catalytic Properties for Ethylene Polymerization" Organometallics, vol. 23, pp. 540-546, 2004.
Turner et al., "Facile resolution of constrained geometry indenyl-phenoxide ligation", Chem. Commun. pp. 1034-1035, 2003.
Christie et al., "Novel Routes to Bidentate Cyclopentadienyl-Alkoxide Complexes of Titanium: Synthesis of ($n^5$-o-$C_5R^1_4CHR^2CH_2CR^3R^4O)TiC1_2$", Organometallics, vol. 18, pp. 348-359, 1999.
Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group" Organometallics, vol. 17, pp. 1652-1654, 1998.
Rau et al., "Synthesis and application in high-pressure in high-pressure polymerization of a titanium complex with a linked cyclopentadienyl-phenoxide ligand", Journal of Organometallic Chemistry, vol. 608, pp. 71-75, 2000.
Guo et al., "Bimetallic Catalysis for Styrene Homopolymerization and Ethylene-Styrene Copolymerization. Exceptional Comonomer Selectivity and Insertion Regiochemistry", J. Am. Chem, Soc., vol. 126, pp. 6542-6543, 2004.

* cited by examiner

*Primary Examiner*—Porfirio Nazario Gonzalez
(74) *Attorney, Agent, or Firm*—Lerner, David, Littenberg, Krumholz & Mentlik, LLP

(57) ABSTRACT

The present invention provides a novel mononuclear transition metal compound, a novel binuclear transition metal compound, a novel organic amine or phosphorous compound, and a method for preparing the same. The mononuclear transition metal compound according to the present invention is configured such that a cyclopentadienyl group and an amido or phosphorous group are bridged via a phenylene bridge. The binuclear transition metal compound according to the present invention is configured such that the two bridged mononuclear transition metal compounds configured such that a cyclopentadienyl group and an amido or phosphorous group are bridged via a phenylene bridge are linked via a bridging group located at the phenylene bridge. According to the present invention, the mononuclear transition metal compound, the binuclear transition metal compound, the organic amine or phosphorous compound can be prepared in a simple manner by using suzuki-coupling reaction with a high yield.

11 Claims, No Drawings

TRANSITION METAL COMPLEXES AND PREPARATION METHODS THEREOF

TECHNICAL FIELD

The present invention relates to a novel transition metal compound, to an intermediate compound, and to a method for preparing the same. Specifically, the present invention relates to a novel mononuclear transition metal compound in which a cyclopentadienyl group and an amido or phosphorous group are bridged via a phenylene bridge, to a novel binuclear transition metal compound in which the two bridged novel mononuclear transition metal compounds are linked via a bridging group located at the phenylene bridge, to an intermediate compound for preparing the transition metal compound, and to a simple and easy method for preparing the same.

This application claims priority benefits from Korean Patent Application Nos. 10-2005-0135900 and 10-2006-0067117, filed on Dec. 30, 2005 and Jul. 18, 2006, respectively, the entire contents of which are fully incorporated herein by reference.

BACKGROUND ART

The Dow Chemical Company announced $[Me_2Si(Me_4C_5)NtBu]TiCl_2$ (Constrained-Geometry Catalyst, which will be simply referred to as CGC) in the early 1990's (U.S. Pat. No. 5,064,802), wherein in the copolymerization reaction of ethylene and alpha-olefin, excellent characteristics that the CGC has, as compared with per se known metallocene catalysts can be usually classified into the two categories: (1) it produces a high molecular weight polymer with high activity even at a high polymerization temperature, and (2) it yield very excellent copolymerization of an alpha-olefin having high steric hindrance, such as 1-hexene and 1-octene. In addition, upon polymerization reaction, there have been gradually several characteristics of CGC, and thus extensive studies to synthesize a derivative of CGC for use as a polymerization catalyst have been made in the academic and industrial fields.

As one approach, there have been trials for synthesis of metal compounds to which various bridges and nitrogen substituents instead of silicon bridges are introduced, and polymerization using the same. Some representative examples of recently known metal compounds include the followings (*Chem. Rev.* 2003, 103, 283):

(1)

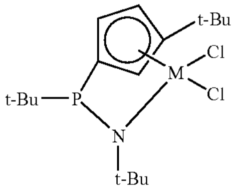

(2)

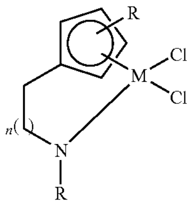

-continued (3)

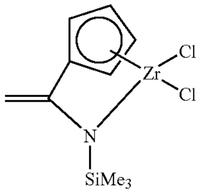

(4)

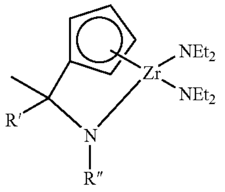

To the above-listed compounds, a phosphorous bridge (1), an ethylene or propylene bridge (2), a methylidene bridge (3), and a methylene bridge (4) are each introduced, instead of the silicon bridges in the CGC structure. However, when they are used for ethylene polymerization, or copolymerization with an alpha-olefin, they had no excellent results regarding the activity or the copolymerization performances, as compared with CGC.

As another approach, there have trials for synthesis of many compounds comprising an oxido ligand instead of the amido ligand of the CGC, and sometimes polymerization using the same. Examples thereof are summarized as follows:

(5)

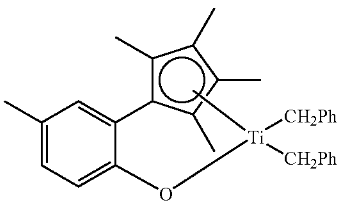

(6)

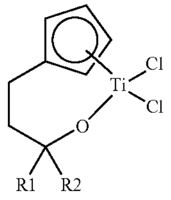

(7)

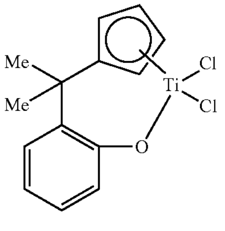

-continued

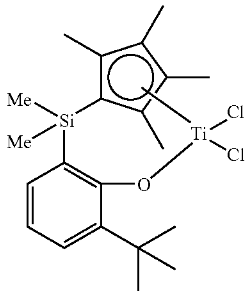

(8)

The compound (5) is characterized in that a Cp derivative and an oxido ligand are bridged via an orthophenylene group, as disclosed by T. J. Marks, et al. (*Organometallics* 1997, 16, 5958). Also, a compound having the same bridge and polymerization using the same are disclosed by Mu, et al. (Organometallics 2004, 23, 540). Further, an indenyl ligand and an oxido ligand are bridged via the same orthophenylene group, as disclosed by Rothwell, et al. (*Chem. Commun.* 2003, 1034). The (6) is characterized in that a cyclopentadienyl ligand and an oxido ligand are bridged through three carbons, as disclosed by Whitby, et al. (*Organometallics* 1999, 18, 348), and these catalysts are reported to exhibit activity on syndiotactic polystyrene polymerization. Further, similar compounds are also reported by Hessen, et al. (*Organometallics* 1998, 17, 1652). The compounds shown in (7) is characterized in that it exhibits activity on ethylene and ethylene/1-hexene copolymerization at a high temperature and a high pressure (210° C., 150 MPa), as disclosed by Rau, et al. (*J. Organomet. Chem.* 2000, 608, 71). Further, synthesis of a catalyst having the similar structure (8), and polymerization using the catalyst at a high temperature and a high pressure were filed in the patent application by Sumitomo Corp. (U.S. Pat. No. 6,548,686).

Recently, a compound having two metal positions was developed, and has been employed as a polymerization catalyst since then. U.S. Pat. No. 6,153,776 describes a binuclear metal compound in which two compounds in the CGC form are bridged via a cyclopentadienyl (Cp) group, an Si bridge, or an N substituent group, and a method for preparing an olefin polymer using the same. Marks, et al., [*J. Am. Chem. Soc.,* 2004, 126, 6542-6543] describes that if a binuclear Ti metal compound in which two compounds in the CGC form are bridged via a $—CH_2CH_2—$ group is used for styrene homopolymerization and ethylene/styrene copolymerization reactions, the polymerization activity is more excellent than that of the conventionally used CGC compounds. Further, Marks, et al, describes an example in which a Ti compound and a Zr compound, each in the CGC form, are sequentially bridged to prepare a binuclear Ti/Zr metal compound, and this compound can be used for an ethylene homopolymerization reaction for preparation of polyethylene having a branch, even without comonomers. Accordingly, the above prior arts show that by using a binuclear metal compound for an olefin polymerization reaction, a polyolefin having more excellent activity and novel physical properties can be prepared, as compared with when using the conventionally used single metal compound.

However, in spite of the above trials, only few catalysts are substantially in use for commercial plants. Thus, there is still a need of development of a catalyst having a novel structure, and preparation of a polymer using the same. Particularly, the conventional binuclear catalyst compounds still have structures in the CGC form, and the method for preparing the same is complex and the production yield is low. Therefore, there is still a desire of a binuclear transition metal compound having a novel structure, which is capable of exhibiting a catalytic activity, and a method for simply preparing the same in high yield.

DISCLOSURE OF INVENTION

Technical Problem

It is a first object of the present invention to provide a novel mononuclear transition metal compound having excellent catalytic activity and capable of being easily prepared.

It is a second object of the present invention to provide a novel binuclear transition metal compound having excellent catalytic activity and capable of being easily prepared.

It is a third object of the present invention to provide a novel organic amine or organic phosphorus compound usable as an intermediate for preparing the novel mononuclear and the binuclear transition metal compounds.

It is a fourth object of the present invention to provide a simple and easy method for preparing the novel mononuclear or the binuclear transition metal compound.

Technical Solution

In order to accomplish the first object, the present invention provides a novel mononuclear transition metal compound in which a cyclopentadienyl group and an amido or phosphorous group are bridged via a phenylene bridge.

In order to accomplish the second object, the present invention provides a novel binuclear transition metal compound in which the two bridged mononuclear transition metal compounds having a cyclopentadienyl group and an amido or phosphorous group bridged via a phenylene bridge are linked via a bridging group located at the phenylene bridge.

In order to accomplish the third object, the present invention provides a novel organic amine or organic phosphorus compound comprising a phenylene bridge containing an amido or phosphorous group.

In order to accomplish the fourth object, the present invention provides a method for preparing the novel mononuclear or the binuclear transition metal compound by using a Suzuki-Coupling reaction.

ADVANTAGEOUS EFFECTS

The mononuclear transition metal compound of the present invention is configured such that a cyclopentadienyl group and an amido or phosphorous group are bridged via a phenylene bridge. Further, the binuclear transition metal compound of the present invention is configured such the two bridged mononuclear transition metal compounds having a cyclopentadienyl group and an amido or phosphorous group bridged via a phenylene bridge are linked via a bridging group located at the phenylene bridge. Furthermore, according to the present invention, the mononuclear or binuclear transition metal compound can be prepared with high yield in a simple manner by using a Suzuki-Coupling reaction.

BEST MODE FOR CARRYING OUT THE INVENTION

Hereinafter, the present invention will be described in detail.

The present invention provides a mononuclear transition metal compound of the following formula 1:

[Formula 1]

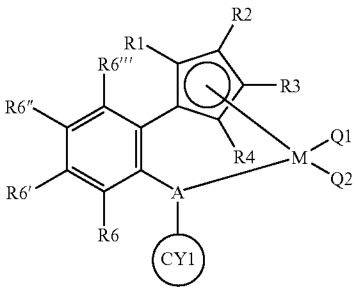

wherein

R1 to R4 are each independently a hydrogen atom; an alkyl radical having 1 to 20 carbon atoms; an aryl radical having 6 to 20 carbon atoms; an alkenyl radical having 2 to 20 carbon atoms; an alkylaryl radical having 7 to 20 carbon atoms; an arylalkyl radical having 7 to 20 carbon atoms radical; or a metalloid radical of a Group 14 metal substituted with hydrocarbyl having 1 to 30 carbon atoms; at least two of R1 to R4 may be bonded together by an alkylidene radical containing an aryl or alkyl radical having 1 to 20 carbon atoms to form a ring;

R6 to R6''' are each independently a hydrogen atom; a halogen radical; an alkyl radical having 1 to 20 carbon atoms; or an aryl radical having 6 to 20 carbon atoms; and at least two of R6 to R6''' may be bonded together to form a fused ring;

A is a nitrogen or phosphorous atom;

CY1 is an aliphatic ring having 5 to 20 carbon atoms;

Q1 and Q2 are each independently a halogen radical; an alkylamido radical having 1 to 20 carbon atoms; an arylamido radical having 6 to 20 carbon atoms; an alkyl radical having 1 to 20 carbon atoms; an alkenyl radical having 2 to 20 carbon atoms; an aryl radical having 6 to 20 carbon atoms; an alkylaryl radical having 7 to 20 carbon atoms; an arylalkyl radical having 7 to 20 carbon atoms; or an alkylidene radical having 1 to 20 carbon atoms; and M is a Group 4 transition metal.

In the formula 1, it is preferable that R1 and R4, R2 and R3, and R6 to R6''' are the same to each other.

The mononuclear transition metal compound according to the present invention has an amido or phosphorous ligand bridged via a phenylene bridge, unlike the conventional transition metal compounds which have ligands containing cyclopentadiene, and thus the mononuclear transition metal compound can stably maintain a rigid pentagon ring structure which allows easier approach to a monomer having large structurally steric hindrance. Further, a catalyst composition comprising the mononuclear transition metal compound exhibits high activity and high comonomer reactivity, and allows preparation of a polyolefin polymer having a double composition distribution.

Specifically, in the mononuclear transition metal compound of the formula 1, the cyclopentadienyl group (Cp), and the amido group or phosphorous group are linked via a phenylene bridge, and thus there is tendency that structurally the Cp-M-A angle keeps narrow, while the Q1-M-Q2 angle for approach of the monomers keeps wide. Further, to be contrary with the CGC structure having a linkage via a silicon bridge, for example, the compound structure represented by the formula 1 has a stable and rigid pentagon ring structure having metal positions with a cyclopentadienyl ring (Cp), a phenylene bridge, and a nitrogen or phosphorous atom. Thus, it is possible that these compounds are reacted with a cocatalyst such as methylaluminoxane and $B(C_6F_5)_3$ for activation, and then used in the olefin polymerization, and it is also possible that even at a high polymerization temperature, a polyolefin having the characteristics such as high activity, high molecular weight, and high copolymerizability is produced. In particular, in the structural characteristics of the catalyst, an ultra-low-density polyolefin copolymer having a density less than 0.910 g/cc due to potential introduction of a large amount of alpha-olefins, as well as a linear low-density polyethylene having a density of about 0.910 to 0.930 g/cc, can be prepared. Further, various substituents can be introduced to a the cyclopentadienyl ring, the nitrogen or phosphorous atom, and the phenylene ring, wherein the electronic or steric environment surrounding the metal can be easily regulated according to the kinds of the introduced substituents, and thus the structure and the physical properties of the resulting polyolefin can be controlled. The mononuclear transition metal compound according to the present invention is preferably used in the preparation of a catalyst for polymerizing olefin monomers, but not limited thereto. Also, the mononuclear transition metal compound can be employed in any field in which other transition metal compound as described above can be used.

In particular, if the transition metal complex having the structure of the formula 1 is used for olefin polymerization, a polymer having a double composition distribution can be prepared. Specifically, the structure of the aliphatic ring represented by CY1 in the formula 1 is cyclopentyl, cyclohexyl, cycloheptyl, cyclooctyl, or the like, but not limited thereto, and it can be any aliphatic ring having 5 to 20 carbon atoms.

The compound of the formula 1 is preferably a compound of the following formula 2:

[Formula 2]

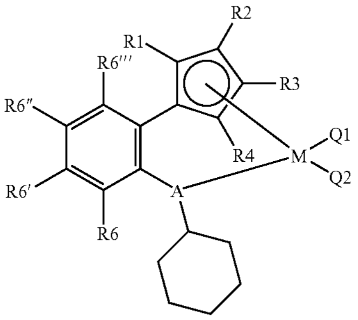

wherein R1 to R4, R6 to R6''', A, Q1, Q2 and M each have the same meanings as defined in the formula 1.

Further, the present invention provides a binuclear transition metal compound of the following formula 3:

[Formula 3]

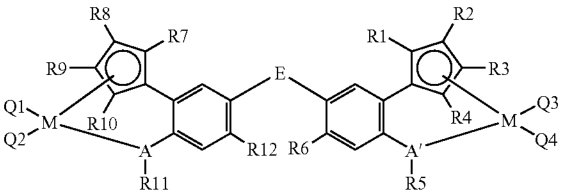

wherein

R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;

R5 and R11 is an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom;

E is a covalent bridging group for bridging two phenylene rings and is an epoxy group; an epithio group; a carbonyl group; a silane group; a disilane group; a substituted or unsubstituted hydrocarbylene group having 1 to 60 carbon atoms; or a substituted or unsubstituted Group 4B, 5B or 6B element-containing heterohydrocarbylene group having 1 to 60 carbon atoms;

Q1 to Q4 are each independently a halogen radical; an alkylamido radical having 1 to 20 carbon atoms; an arylamido radical; an alkyl radical having 1 to 20 carbon atoms; an alkenyl radical; an aryl radical; an alkylaryl radical; an arylalkyl radical; or an alkylidene radical having 1 to 20 carbon atoms; and M is a Group 4 transition metal.

In the formula 3, R1, R4, R7 and R10; R2, R3, R8 and R9; R6 and R12; and R5 and R11 are preferably the same to each other.

The binuclear transition metal compound according to the present invention is configured such that a cyclopentadienyl group and an amido or phosphorous group are bridged via a phenylene bridge, and two single metal compounds formed by the binding of the metal positions are linked by a bridging group located on the phenylene bridge, such as —$CH_2$—, —O—, and —S— groups. Further, in the present invention, a novel ligand and a binuclear transition metal compound can be prepared in a simple manner with high yield, by using a suzuki-coupling reaction for linking the cyclopentadienyl group and the phenylene bridge, to provide various electronic or steric environment surrounding the metal.

Specifically, in the binuclear transition metal compound represented by the formula 3, two single metal compounds are linked by a bridging group located on the phenylene bridge, and the metal compounds are configured that the cyclopentadienyl derivative (Cp) and the amido group or phosphorous group are linked by the phenylene bridge. Thus, it is characterized in structurally the Cp-M-A angle keeps narrow, while the Q1-M-Q2 and Q3-M-Q4 angles for approach of the monomers keeps wide. To be contrary with the CGC structure having a linkage via a silicon bridge, in the compound structure represented by the formula 3, a Cp, a phenylene bridge, and a nitrogen or phosphorous atom constitute a stable and rigid pentagon ring structure with the metal positions, and the reactivities of the two metal positions are highly likely to affect with each other. Therefore, it is expected that it is possible that if the binuclear transition metal compound of the present invention are reacted with a cocatalyst such as methylaluminoxane and $B(C_6F_5)_3$ for activation, and then used in the olefin polymerization, polyolefins having unique structures and physical properties are produced, as compared with conventional single metal compounds. Further, various substituents can be introduced to a the cyclopentadienyl ring, the nitrogen or phosphorous atom, and the phenylene ring, wherein the electronic or steric environment can be easily regulated according to the kinds of the introduced substituents, and thus the structure and the physical properties of the resulting polyolefin can be controlled. Further, also in the case of the binuclear transition metal compound, a polyolefin with a double composition distribution can be prepared. The binuclear transition metal compound according to the present invention is preferably used for the preparation of a catalyst for polymerizing olefin monomers, but not limited thereto. Further, it can be employed in any field in which the transition metal compound as described above can be used.

In the present invention, a compound represented by the following formula 4 is preferred as a compound which is desirable for easy regulation of the electronic or steric environments around the metal in the formula 3:

[Formula 4]

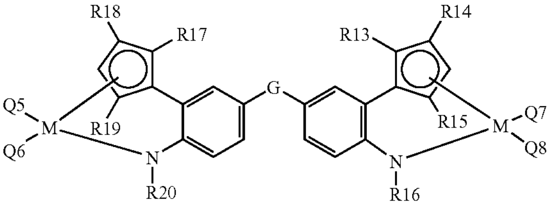

wherein

R13 to R15, and R17 to R19 are each independently a hydrogen atom; or an alkyl radical having 1 to 20 carbon atoms; an aryl radical; or a silyl radical;

R16 and R20 are each independently an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; or an arylalkyl radical;

Q5 to Q8 are each independently a halogen radical; an alkylamido radical having 1 to 20 carbon atoms; an arylamido radical; or an alkyl radical having 1 to 20 carbon atoms;

G is an epoxy group; an epithio group; a carbonyl group; a heterohydrocarbylene group having 1 to 60 carbon atoms, substituted with a substituent containing an oxygen or nitrogen atom; or —$C(R21)_2$— (wherein R21 is hydrogen, or alkyl having 1 to 20 carbon atoms; aryl; silyl; alkenyl having 2 to 20 carbon atoms; alkylaryl; or arylalkyl); or a metalloid radical of a Group 14 metal substituted with hydrocarbyl; and M is a Group 4 transition metal.

As G, the hydrocarbylene group having 1 to 60 carbon atoms is preferably a hydrocarbylene group having 10 or less carbon atoms such as methylidene, ethylidene, propylidene, butylidene, and pentylidene.

The compound of the formula 4 is preferably a compound represented by the following formula 5:

[Formula 5]

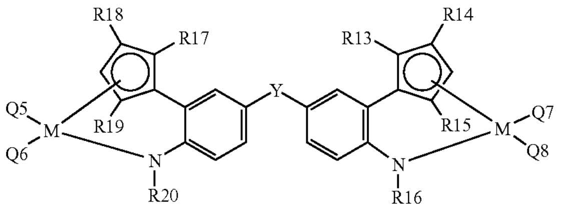

wherein

Y is $—CH_2—$, $—C(CH_3)_2—$, $—C(=O)—$, $—C(=NR22)-$, $—O—$ or $—S—$ (wherein R22 is a hydrogen atom; an alkyl radical having 1 to 20 carbon atoms; an aryl radical; a silyl radical; an alkenyl radical having 2 to 20 carbon atoms; an alkylaryl radical; or an arylalkyl radical;

R13 to R20, Q5 to Q8, and M each have the same meanings as defined in the formula 4.

The compound of the formula 1 is preferably a compound represented by the following formula 6:

[Formula 6]

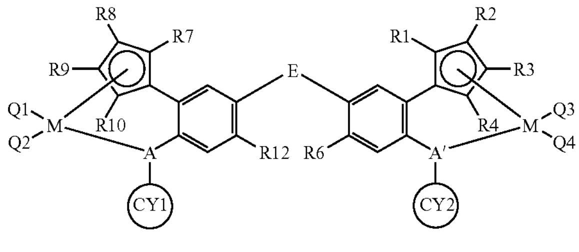

wherein

R1 to R4, R6 to R10, R12, Q1 to Q4, A, A', E and M each have the same meanings as defined in the formula 3, and CY1 and CY2 are each independently an aliphatic ring having 5 to 20 carbon atoms.

The compound of the formula 6 is preferably a compound represented by the following formula 7:

[Formula 7]

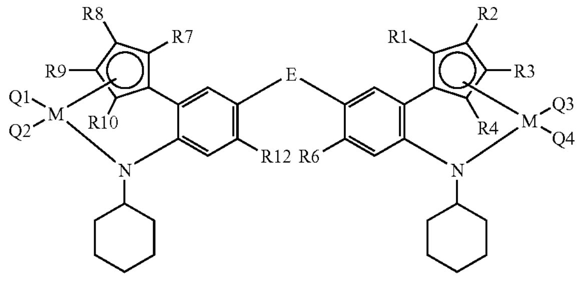

wherein R1 to R4, R6 to R10, R12, Q1 to Q4, E and M each have the same meanings as defined in the formula 3.

In the present invention, the binuclear transition metal compound of the formula 3 is particularly preferably represented by one of the following structures:

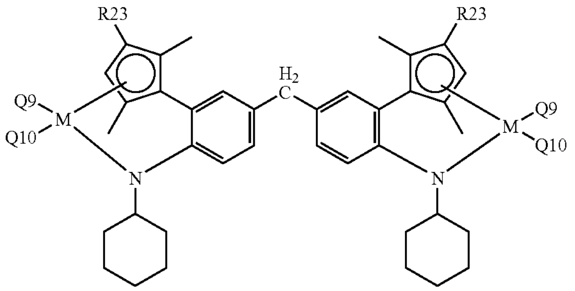

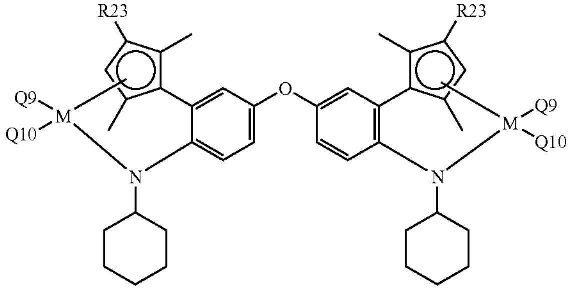

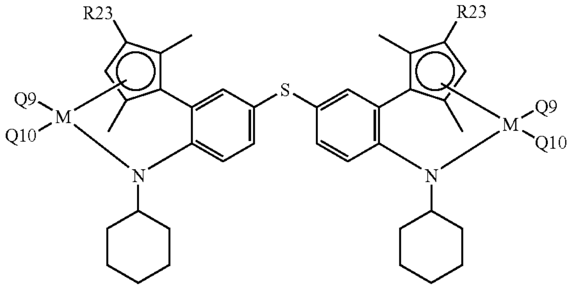

In the above structures,

R23 is selected from hydrogen and a methyl radical, and

Q9 and Q10 are each independently selected from methyl, dimethylamido, diethylamido and chloride radicals.

In the present specification, each of the substituents will be described in detail.

The alkyl radical having 1 to 20 carbon atoms may be linear or branched, and examples thereof include a methyl group, an ethyl group, a propyl group, an isopropyl group, a butyl group, a tert-butyl group, a pentyl group, a hexyl group, and a heptyl group, but are not limited thereto.

The aryl radical preferably contains 6 to 20 carbon atoms, and specifically examples thereof include a phenyl group, a naphthyl group, an anthracenyl group, a biphenyl group, a pyrenyl group and a perylenyl group, but are not limited thereto.

Examples of the silyl radical include trimethylsilyl, triethylsilyl, tri-iso-propylsilyl, tri-t-butylsilyl, and triphenylsilyl, but are not limited thereto.

The alkenyl radical may be linear or branched, and preferably contains 2 to 20 carbon atoms. Specifically, examples thereof include vinyl, 1-propenyl, 2-propenyl, isopropenyl, 1-butenyl, 2-butenyl, 3-butenyl, 1-pentenyl, 2-pentenyl, 3-pentenyl, 3-methyl-1-butenyl, 1,3-butadienyl, 1-octenyl, 1-decenyl, and 1-octadecenyl, but are not limited thereto.

The alkylaryl radical means aryl substituted with the above-described alkyl, and preferably contains 7 to 20 carbon atoms.

The arylalkyl radical means alkyl substituted with the above-described aryl, and preferably contains 7 to 20 carbon atoms.

Examples of the Group 4 transition metal include Ti, Zr and Hf.

The hydrocarbyl radical means a monovalent substituent formed by the removal of a hydrogen atom from hydrocarbon, preferably contains 1 to 60 carbon atoms, more preferably 1 to 30 carbon atoms. Specifically, examples thereof include alkyl, alkenyl, alkynyl, aryl, alkylaryl, and arylalkyl, but are not limited thereto.

The metalloid comprehensively refers to a metal having similar properties to both metals and non-metals. Examples thereof include boron, silicon, arsenide, antimony, and tellurium, but are not limited thereto.

In the present invention, the substituent of the substituted hydrocarbylene group or the substituted heterohydrocarbylene group is preferably halogen, alkyl having 1 to 20 carbon atoms, alkoxy having 1 to 20 carbon atoms, or aryl having 6 to 20 carbon atoms, but are not limited thereto. Any other substituent available in the art can be used for this.

The present invention provides a novel organic amine or organic phosphorus compound represented by the following formulae 8 to 12, as a ligand coordinated to the metal in the transition metal compound:

[Formula 8]

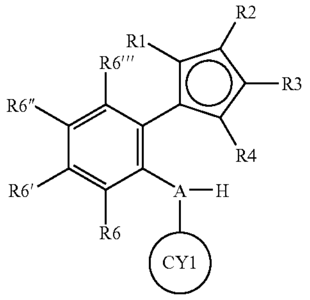

wherein R1 to R4, R6 to R6''', A and CY1 each have the same meanings as defined in the formula 1.

[Formula 9]

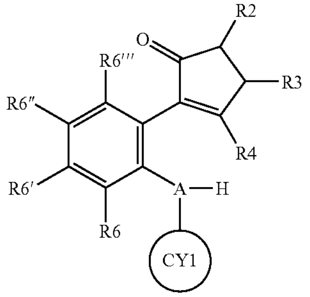

wherein R2 to R4, R6 to R6''', A and CY1 each have the same meanings as defined in the formula 1.

[Formula 10]

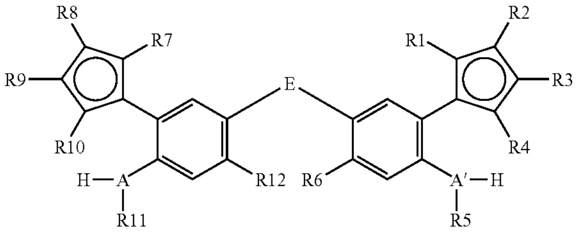

wherein R1 to R12, A, A' and E each have the same meanings as defined in the formula 3.

[Formula 11]

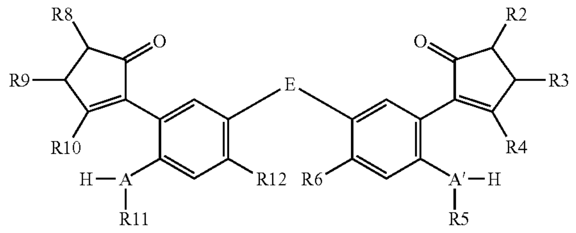

wherein R2 to R6 and R8 to R12, A, A' and E each have the same meanings as defined in the formula 3.

[Formula 12]

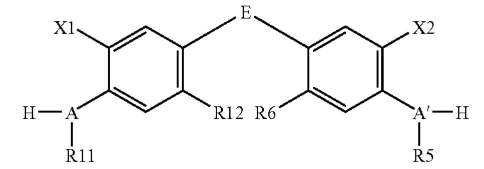

wherein, R5, R6, R11, R12, A, A' and E each have the same meanings as defined in the formula 3, and X1 and X2 are each independently a halogen atom.

If the compound of the formula 8 is coordinated to a metal, a phenylene bridge is formed, and nitrogen or phosphorus and cyclopentadiene are coordinated to the metal. Further, if the compound of the formula 10 is coordinated to two metals, two phenylene bridges are each formed, and nitrogen and cyclopentadiene are coordinated to the metals. The organic amine or organic phosphorus compounds are preferably used as the ligand of the mononuclear or binuclear transition metal compound according to the present invention, but the scope of the present invention is not limited thereto. The compounds of the present invention can be used in any other fields.

The present invention also provides a novel method for preparing a mononuclear or binuclear transition metal compound represented by the formulae 1 to 7 in easy and various manners. Specifically, the present invention uses carbon-carbon coupling reaction (Suzuki Reaction) in the presence of a Pd metal catalyst in order to prepare a cyclopentadienyl ligand having a phenylene bridge represented by the formula 8, or a cyclopentadienyl ligand having two phenylene bridges represented by the formula 10. The Suzuki reaction is generally a representative method well known in the organic chemistry, used for forming a C—C bond. By using this reaction, it is possible to prepare a monocyclopentadienyl ligand represented by the formula 8, or two monocyclopentadienyl ligands represented by the formula 10, each having various substituents introduced to cyclopentadienyl, nitrogen or phosphorous, and around phenylene bridge, and accordingly it is possible to prepare a mononuclear or binuclear transition metal compound represented by the formulae 1 to 7 with the regulated electronic or steric hindrance around metal.

According to one embodiment of the present invention, there is provided a method for preparing a mononuclear transition metal compound, comprising the steps of:

a) reacting a benzene compound having substituted with a —$NH_2$ group or —$PH_2$ group with an organic compound represented by the following formula 13 to prepare a halide of the benzene compound;

b) reacting the halide of the benzene compound with a boronic acid compound represented by the following formula 14 to prepare a compound represented by the following formula 9;

c) reacting the compound represented by the formula 9 with an R'Li or R'MgX compound, and then adding an acid thereto to prepare a compound represented by the formula 8, wherein R' is a hydrogen atom; an alkyl radical having 1 to 20 carbon atoms; an aryl radical; an silyl radical; an alkenyl having 2 to 20 carbon atoms; an alkylaryl radical; an arylalkyl radical; or a metalloid radical of a Group 14 metal substituted with hydrocarbyl; and X is a halogen atom;

d) reacting the compound represented by the formula 8 with a base to prepare a lithium compound represented by the following formula 15; and e) reacting the lithium compound represented by the formula 15 with an in-situ mixture alkyllithium and $MX_4$ (wherein X=halogen; and M is a Group 4 transition metal) to prepare a compound represented by the following formula 1:

[Formula 1]

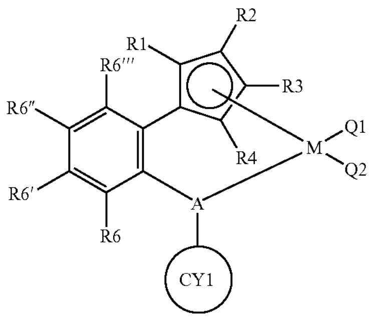

wherein R1 to R4, R6 to R6''', A, CY1, M, Q1 and Q2 each have the same meanings as described above;

[Formula 8]

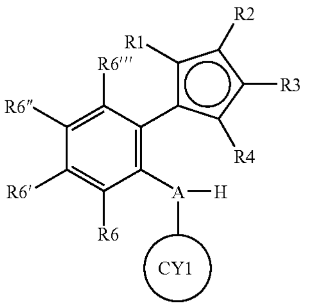

wherein R1 to R4, R6 to R6''', A and CY1 each have the same meanings as defined in the formula 1;

[Formula 9]

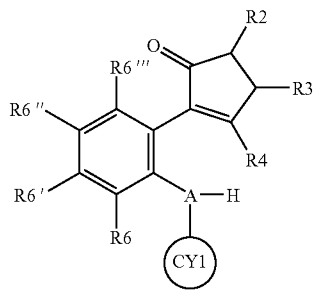

wherein R2 to R4, R6 to R6''', A and CY1 each have the same meanings as defined in the formula 1;

[Formula 13]

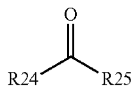

wherein

R24 and R25 are each independently an aryl or alkyl radical having 1 to 20 carbon atoms, and R24 and R25 may be bonded to each other;

[Formula 14]

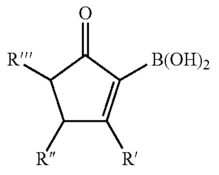

wherein

R', R'' and R''' are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; and

[Formula 15]

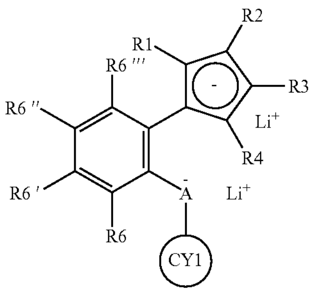

wherein R1 to R4, R6 to R6''', A and CY1 each have the same meanings as defined in the formula 1.

According to another embodiment of the present invention, there is provided a method for preparing a mononuclear transition metal compound, comprising the steps of:

a) reacting a benzene compound having substituted with a —$NH_2$ group or —$PH_2$ group with an organic compound represented by the above formula 13 to prepare a halide of the benzene compound;

b) reacting the halide of the benzene compound with a boronic acid compound represented by the above formula 14 to prepare a compound represented by the following formula 9;

c) reacting the compound represented by the formula 9 with an R'Li or R'MgX compound, and then adding an acid thereto to prepare a compound represented by the formula 8, wherein R' is a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; and X is a halogen atom;

d') reacting the compound represented by the formula 8 with a metal compound represented by the following formula 16, and then adding a $(CH_3)_nSiX_{4-n}$ (wherein X a halogen atom; and n=0, 1, 2 or 3) compound thereto to prepare a compound represented by the above formula 1:

$M(D(R26)_2)_4$ [Formula 16]

wherein M is a Group 4 transition metal, R26 is an aryl or alkyl radical having 1 to 20 carbon atoms, and D is a nitrogen or phosphorous atom.

According to another embodiment of the present invention, there is provided a method for preparing a binuclear transition metal compound, comprising the steps of:

a) reacting a compound represented by the following formula 17 with a compound represented by the formula 13 to prepare a compound represented by the following formula 12;

b) reacting the compound represented by the following formula 12 with a boronic acid compound represented by the formula 14 to prepare a compound represented by the following formula 11;

c) reacting the compound represented by the formula 11 with an R'Li or R'MgX compound, and then adding an acid thereto to prepare a compound represented by the formula 10, wherein R' is a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; and X is a halogen atom;

d) reacting the compound represented by the formula 10 with a base to prepare a dilithium compound represented by the following formula 18; and e) reacting the dilithium compound represented by the formula 18 with an in-situ mixture alkyllithium and $MX_4$ (wherein X=halogen; and M is a Group 4 transition metal) to prepare a compound represented by the following formula 3:

[Formula 3]

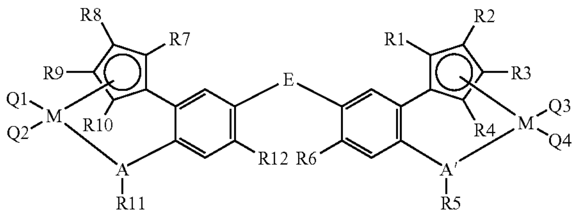

wherein R1 to R12, A, A', E, Q1 to Q4 and M each have the same meanings as described above;

[Formula 10]

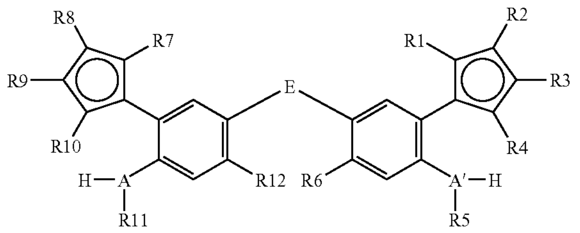

wherein R1 to R12, A, A' and E each have the same meanings as defined in the formula 3;

[Formula 11]

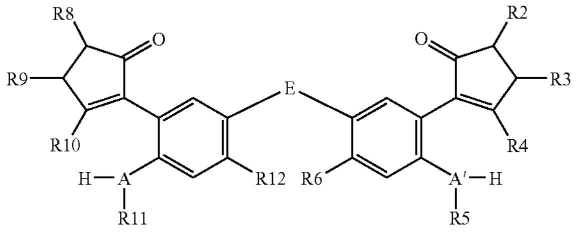

wherein R2 to R6 and R8 to R12, A, A' and E each have the same meanings as defined in the formula 3;

[Formula 12]

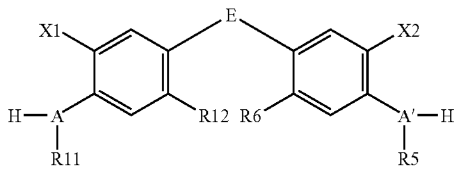

wherein R5, R6, R11, R12, A, A' and E each have the same meanings as defined in the formula 3, and, X1 and X2 are each independently a halogen atom;

[Formula 17]

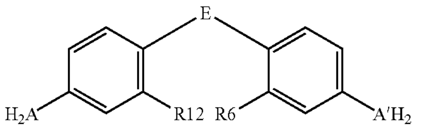

wherein R6, R12, A, A' and E each have the same meanings as defined in the formula 3;

[Formula 18]

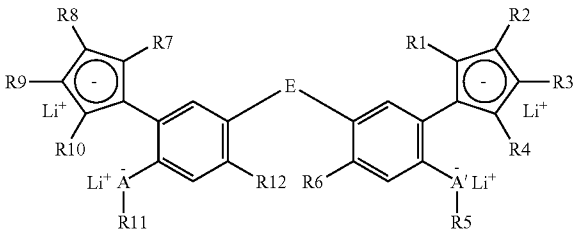

wherein R1 to R12, A, A' and E each have the same meanings as defined in the formula 3.

Among the above-described methods for preparing a binuclear transition metal compound according to the present invention, a method for preparing a binuclear transition metal compound wherein A and A' are both N can be illustrated by the following reaction scheme 1.

[Reaction scheme 1]

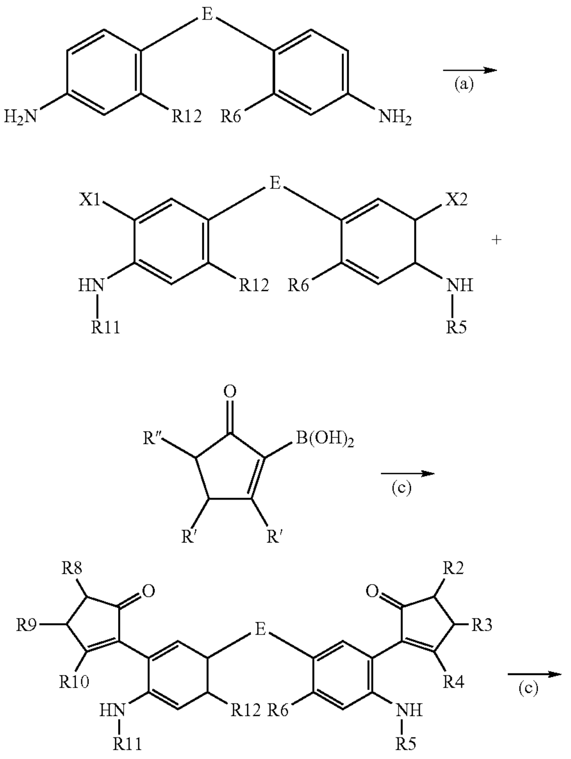

-continued

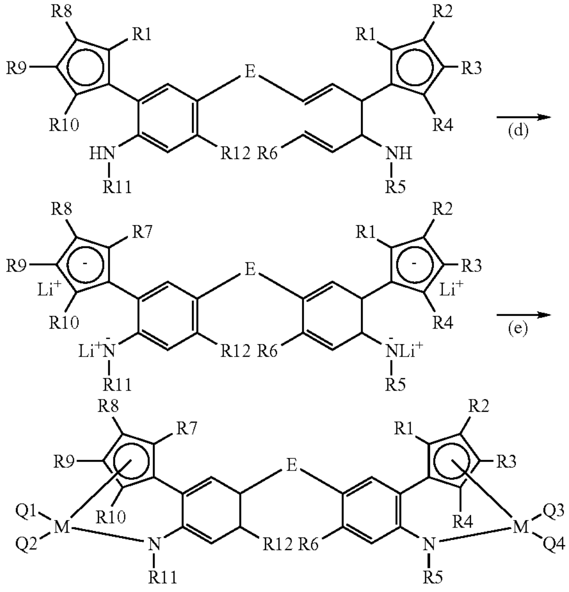

wherein R1 to R12, E, M, Q1 to Q4, R', R'' and R''' each have the same meanings as described above.

Specifically, each of the steps in the method for preparing a binuclear transition metal compound according to the present invention will be described.

In the a) step, a compound represented by the formula 12 can be prepared by reacting a dianiline compound represented by the formula 17 and a compound represented by the formula 13, treating the product compound with a reducing agent such as $NaBH_4$ and $LiAlH_4$, and then reacting the product with a halogen compound such as $Br_2$.

In b) step, boronic acid compounds represented by the formula 14 can be prepared by reacting an α,β-unsaturated ketone compound with a boron triester compound in THF or an ether solvent, and treating the product with an acid. Then, compounds represented by the formula 11 having various diamine-based structures can be prepared by subjecting the boronic acid compound represented by the formula 14 and a halide of dianiline represented by the formula 12 in the presence of a palladium catalyst to "suzuki coupling" reaction. The palladium catalyst usable herein is a phosphine compound represented by the formula 19, as conventionally well known. A preferable compound for use in the present invention is tetrakis(triphenylphosphine)palladium.

[Formula 19]

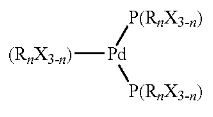

wherein R is each independently alkyl or aryl; X is a halogen atom; and n is an integer of 0 to 3.

In the c) step, a compound represented by the formula 10 can be prepared by reacting the compound represented by the formula 11 with an R'Li or R'MgX compound at a low temperature, preferably 0° C. or lower, and then treating the product with an acid. In this step, in order to improve the reactivity of the R'Li or R'MgX compound, a metal Lewis acid compound such as $CeCl_3$ can be incorporated. Examples of the R' usable herein is a hydrogen atom; alkyl having 1 to 20 carbon atoms, aryl or silyl; alkenyl having 2 to 20 carbon atoms, alkylaryl or arylalkyl; or a metalloid radical of a Group 14 metal substituted with hydrocarbyl, more preferably an alkyl having 1 to 10 carbon atoms or aryl radical, and most preferably methyl, n-butyl, n-hexyl, n-octyl, t-butyl, phenyl, benzyl or (trimethyl)silylmethyl.

In the d) step, a solid compound is prepared by treating the ligand represented by the formula 10 with a base in a solvent such as THF and diethyl ether. Herein, as the base, alkyllithium can be used, and specifically a strong base such as n-BuLi can be used.

A tetralithiated solid compound is prepared by treating the ligand represented by the formula 10 with a 4 equivalents of n-BuLi. Thereafter, in the e) step, a $Me_2MCl_2$ (solvent)$_n$ (wherein M is Ti or Zr, the solvent is THF or $Et_2O$, and n is 1 to 2) compound can be prepared by the reaction of a 2 equivalents of Group 4 metal tetrachloride, and 4 equivalents of an alkyllithium compound such as MeLi at a temperature as low as −78° C. By in-situ treating the tetralithium salt compound prepared in the d) step with the above compound, compounds represented by the following formula 3 having various substituents are easily prepared. In particular, a Group 4 transition metal compound having Q1 to Q4 directly substituted with an alkyl or aryl group can be obtained with a high yield (70% or more).

According to another embodiment of the present invention, there is provided a method for preparing a binuclear transition metal compound, comprising the steps of:

a) reacting a compound represented by the formula 17, and a organic compound represented by the formula 13 to prepare a compound represented by the formula 12;

b) reacting the compound represented by the formula 12, and a boronic acid compound represented by the formula 14 to prepare a compound represented by the formula 11;

c) reacting the compound represented by the formula 11 with an R'Li or R'MgX compound, and then adding an acid thereto to prepare a compound represented by the formula 10, wherein R' is a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; and X is a halogen atom; and d') reacting the compound represented by the formula 10 with a metal compound represented by the formula 16, and then adding a $(CH_3)_nSiX_{4-n}$ (wherein X=a halogen atom; and n=0, 1, 2 or 3) compound thereto to prepare a compound represented by the formula 3.

Among the above-described methods for preparing a binuclear transition metal compound according to the present invention, a method for preparing a binuclear transition metal compound wherein A and A' are N can be illustrated by the following reaction scheme 2.

[Reaction scheme 2]

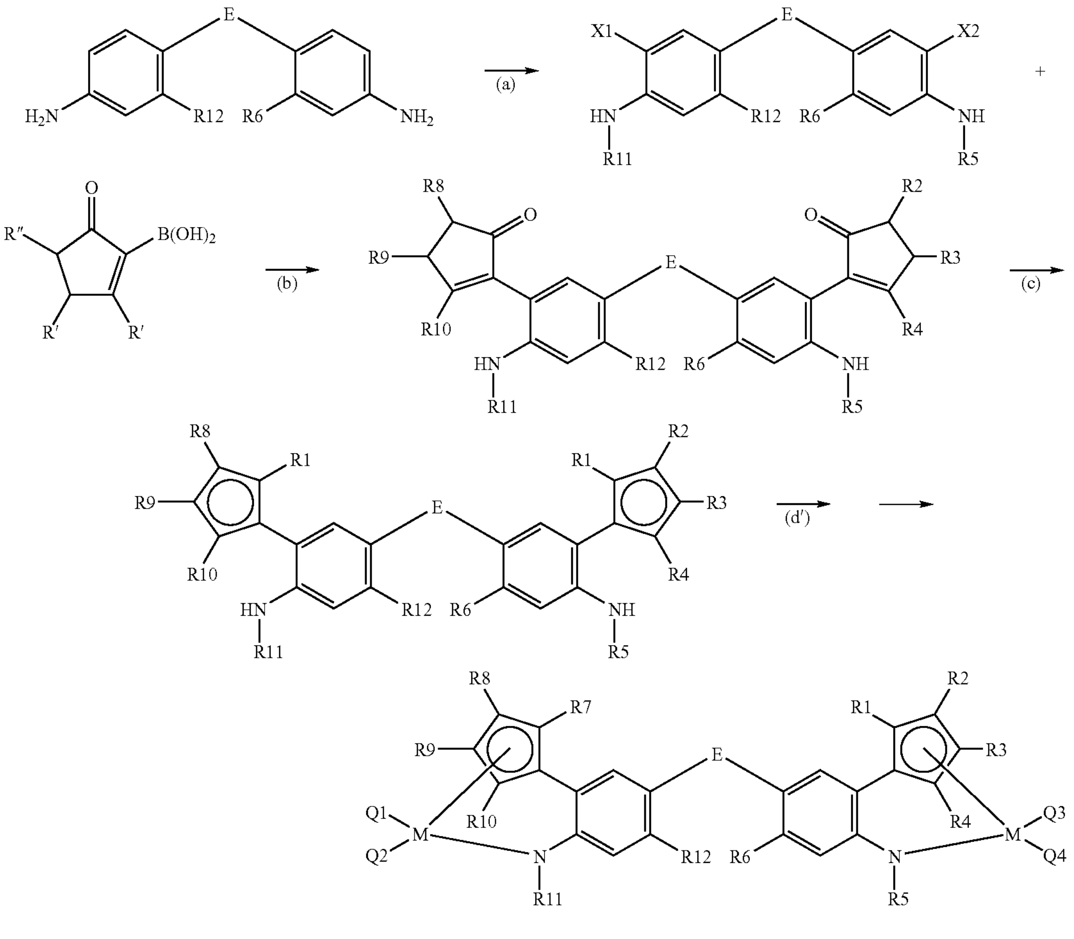

wherein R1 to R12, E, M, Q1 to Q4, R', R'' and R''' each have the same meanings as described above.

In the above-described methods for preparing a binuclear transition metal compound according to the present invention, the (a) to (c) steps are as described above. In the (d') step, a binuclear transition metal compound having a dialkylamido group or a diarylamino group introduced therein is obtained by adding 2 equivalents of a $M(N(R26)_2)_4$ compound to the ligand of the formula 10, and the obtained compound can be treated with 4 equivalents of a $(CH_3)_nSiX_{4-n}$ compound to prepare a compound represented by the formulae 1 to 2a. In particular, by using the process as in the d') step, the binuclear metal compound can be obtained in a high yield of 80% or higher.

Mode for the Invention

Hereinafter, the present invention will be described in more detail by means of Examples, but the scope of the invention is not limited thereto.

Synthesis of Ligand and Metal Compound

The organic reagent and the solvent were purchased from Aldrich Chemical Company and Merck limited, and purified using a standard method for use. In all the steps for synthesis, contact with air and the moisture was avoided to increase the reproductivity of the experiments. In order to demonstrate the structure of the compound, 400 MHz Nuclear Magnetic Resonance Spectrometer (NMR) and X-ray Spectrometer were used for each spectrum and diagrams.

Example 1

2-Dihydroxyboryl-3,4-dimethyl-2-cyclopenten-1-one

To a 1000-mL flask, 2-bromo-3,4-dimethyl-2-cyclopenten-1-one ethylene ketal (57.3 g, 246 mmol) and THF (300 mL) were added and mixed. The flask temperature was lowered to −78° C., and n-BuLi (2.5M in Hexane, 98.3 μL, 245 mmol) was charged thereinto. The temperature was maintained at −78° C., and after 1 hour, boron triisopropyl ester (50.9 g, 270 mmol) was added, and the mixture was stirred for 1.5 hours. Then, the temperature was raised, and at −30° C., it was further stirred for 30 minutes, and then to the flask, 2 N HCl (300 mL) was immediately added. The solution added with the aqueous solution was transferred to a separatory funnel, and an organic layer was extracted from ethanol (300 mL). Then, the organic layer was further extracted from ethanol (300 mL) twice. Water was removed from the combined organic layer over $MgSO_4$, and filtered with a glass filter. The rotary evaporator was used to remove the solvent, thereby obtaining a solid. The obtained solid was pulverized in hexane, and then filtered to obtain 20.3 g of a final product.

$^1H$ NMR ($CDCl_3$): δ1.24 (d, J=3.6 Hz, 3H, $CH_3$), 2.09 (dd, J=19, 2.0 Hz, 1H, $CH_2$), 2.39 (s, 3H, $CH_3$), 2.72 (dd, J=19, 6.8 Hz, 1H, $CH_2$), 2.84-2.86 (m, 1H, CH), 7.29 (s, 2H, OH) ppm. $^{13}C$ {$^1H$} NMR ($CDCl_3$): δ18.01, 18.90, 40.76, 44.22, 197.08, 216.12 ppm. Anal. Calc. ($C_7H_{11}BO_3$): C, 54.60; H, 7.20%. Found: C, 54.40; H, 7.42

Example 2

2-Bromo-N-cyclohexylaniline

Into a 100-mL flask, 2-bromoaniline (1.65 g, 9.56 mmol), cyclohexanone (4.693 g, 47.81 mmol), benzene (9 ml) and molecular sieves (4 Å, 2.0 g) were put. To the flask, a Dean-Stark apparatus was connected for refluxing for 4 days. Then, the solution in the flask was cooled to normal temperature, and then filtered to remove the molecular sieves. The rotary evaporator was used to remove the solvent, and dried in vacuo at 60° C. to obtain an imine compound. The obtained imine compound was dissolved in degassed methanol (28 ml), sodium borohydride (1.08 g, 28.7 mmol) was slowly added under a nitrogen atmosphere, and then the mixture was stirred at normal temperature for 2 hours. Then, to the stirred solution, a 1 N aqueous KOH (20 mL) solution was added. The solution added with the aqueous solution was transferred to a separatory funnel and extracted from methylene chloride (30 mL) twice. Water was removed from the combined organic layer over $MgSO_4$, and filtered with a glass filter. The rotary evaporator was used to remove the solvent, thereby obtaining a residue. The obtained residue was separated by column chromatography to obtain colorless oil (1.43 g, 59%).

$^1H$ NMR ($CDCl_3$): δ 0.99 (t, J=Hz, 2H, Cy), 1.29-1.53 (m, 3H, Cy), 1.72-1.75 (m, 1H, Cy), 1.88-1.84 (m, 2H, Cy), 2.11-2.14 (m, 2H, Cy), 3.36-3.40 (m, 1H, N—CH), 4.34 (br s, 1H, NH), 6.58 (td, J=7.6, 0.8 Hz, 1H, $C_6H_4$), 6.71 (d, J=7.6 Hz, 1H, $C_6H_4$), 7.20 (td, J=7.6, 0.8 Hz, 1H, $C_6H_4$), 7.47 (dd, J=7.6, 1.2 Hz, 1H, $C_6H_4$) ppm. $^{13}C$ {$^1H$} NMR ($CDCl_3$): δ 24.91, 25.94, 33.13, 51.53, 109.62, 111.58, 116.92, 128.16, 132.33, 143.83 ppm. Anal. Calc. ($C_{12}H_{16}BrN$): C, 56.71; H, 6.35; N, 5.51%. Found: C, 56.67; H, 6.58; N, 5.82%

Example 3

N-cyclohexyl-4-methylaniline

Into a 100-mL flask, p-toluidine (3.85 g, 35.9 mmol), cyclohexanone (21.2 g, 0.216 mol), toluene (25 ml) and molecular sieves (4 Å, 7.0 g) were put. The flask was sealed, and the mixture was stirred at 100° C. for 2 days. Then, the molecular sieves were removed, and the resultant was dried in vacuo at 60° C. to obtain an imine compound. The obtained imine compound was dissolved in degassed methanol (28 ml), sodium borohydride (4.08 g, 108 mmol) was slowly added under a nitrogen atmosphere, and then the mixture was stirred at normal temperature for 2 hours. Then, to the stirred solution, a 1 N aqueous KOH (20 mL) solution was added. The solution added with the aqueous solution was transferred to a separatory funnel and extracted from methylene chloride (30 μL) twice. Water was removed from the combined organic layer over $MgSO_4$, and filtered with a glass filter. The rotary evaporator was used to remove the solvent, thereby obtaining a residue. The obtained residue was separated by column chromatography to obtain colorless oil (5.16 g, 76%).

$^1H$ NMR ($C_6D_6$): δ 0.88-0.94 (m, 2H, Cy), 1.04-1.09 (m, 1H, Cy), 1.12-1.21 (m, 2H, Cy), 1.46-1.50 (m, 1H, Cy), 1.55-1.60 (m, 2H, Cy), 1.90-1.93 (m, 2H, Cy), 2.23 (s, 3H, $CH_3$), 3.03 (br s, 1H, NH), 3.04-3.10 (m, 1H, N—CH), 6.45 (d, J=8.0 Hz, 2H, $C_6H_4$), 7.00 (d, J=8.0 Hz, 2H, $C_6H_4$) ppm. $^{13}C$ {$^1H$} NMR($C_6D_6$): δ 20.85, 25.50, 26.50, 33.82, 52.04, 113.82, 125.78, 130.03, 145.60 ppm.

Example 4

2-Bromo-N-cyclohexyl-4-methylaniline

In a 100-mL flask, N-cyclohexyl-4-methylaniline (2.00 g, 10.6 mmol) was dissolved in methylene chloride (20 mL) and a solution of bromine ($Br_2$) (1.69 g, 10.6 mmol) dissolved in methylene chloride (16 ml) was injected at 0° C. for 30 minutes. Then, the solution was further stirred for 2 hours, and a 1 N aqueous KOH (20 mL) solution was added. The solution added with the aqueous solution was transferred to a separatory funnel and extracted from methylene chloride (40 mL) twice. Water was removed from the combined organic layer over $MgSO_4$, and filtered with a glass filter. The rotary evaporator was used to remove the solvent, thereby obtaining a residue. The obtained residue was separated by column chromatography to obtain colorless oil (2.67 g, 94%).

$^1H$ NMR($C_6D_6$): δ 0.98-1.03 (m, 3H, Cy), 1.10-1.16 (m, 3H, Cy), 1.39-1.42 (m, 1H, Cy), 1.53-1.56 (m, 2H, Cy), 1.82-1.85 (m, 2H, Cy), 2.03 (s, 3H, $CH_3$), 3.06-3.08 (m, 1H, N—CH), 4.16 (br d, J=7.2 Hz, 1H, NH), 6.46 (d, J=7.6 Hz, 1H, $C_6H_3$), 6.84 (dd, J=1.6, 7.6 Hz, 1H, $C_6H_3$), 7.23 (d, J=1.6 Hz, 1H, $C_6H_3$) ppm. $^{13}C$ {$^1H$} NMR ($C_6D_6$): δ 20.25, 25.21, 26.29, 33.37, 51.90, 110.25, 112.29, 126.71, 129.24, 133.29, 142.34 ppm.

Example 5

N-Cyclohexyl-4-phenylaniline

The same procedure was carried out in the same manner as in Example 3 except that benzidine was used instead of p-toluidine to obtain a yellow solid compound (65%).

$^1H$ NMR($C_6D_6$): δ 0.84-0.94 (m, 2H, Cy), 1.02-1.21 (m, 3H, Cy), 1.46-1.59 (m, 3H, Cy), 1.88-1.91 (m, 2H, Cy), 3.06-3.11 (m, 1H, N—CH), 3.18 (br s, 1H, NH), 6.49 (d, J=8.0 Hz, 2H, $C_6H_5$), 7.14 (t, J=8.0 Hz, 1H, $C_6H_4$), 7.28 (t, J=8.0 Hz, 2H, $C_6H_5$), 7.49 (d, J=8.0 Hz, 2H, $C_6H_4$), 7.60 (d, J=8.0 Hz, 2H, $C_6H_5$) ppm. $^{13}C$ {$^1H$} NMR ($C_6D_6$): δ 25.43, 26.41, 33.66, 51.70, 113.78, 126.15, 126.59, 128.27, 129.00, 130.10, 142.03, 147.14 ppm.

Example 6

2-Bromo-N-cyclohexyl-4-phenylaniline

The same procedure was carried out in the same manner as in Example 4 except that N-cyclohexyl-4-phenylaniline was used instead of N-cyclohexyl-4-methylaniline to obtain a colorless oil compound (73%).

$^1H$ NMR ($C_6D_6$): δ 0.96-1.05 (m, 2H, Cy), 1.06-1.18 (m, 2H, Cy), 1.23-1.31 (m, 1H, Cy), 1.39-1.44 (m, 1H, Cy), 1.52-1.56 (m, 2H, Cy), 1.79-1.83 (m, 2H, Cy), 3.02-3.11 (m, 1H, N—CH), 4.35 (br d, J=7.2 Hz, 1H, NH), 6.52 (d, J=8.0 Hz, 1H, C H), 7.11 (tt, J=1.6, 8.0 Hz, 1H, $C_6H_5$), 7.21 (t, J=8.0 Hz, 2H, $C_6H_5$), 7.34 (dd, J=2.4, 8.4 Hz, 1H, $C_6H_3$), 7.37 (dd, J=1.2, 8.0 Hz, 2H, $C_6H_5$), 7.78 (d, J=2.4 Hz, 1H, $C_6H_3$) ppm. $^{13}C$ {$^1H$} NMR($C_6D_6$): δ 25.13, 26.20, 33.22, 51.70, 110.72, 112.28, 126.56, 126.62, 127.36, 129.02, 130.93, 131.42, 140.42, 143.67 ppm.

Example 7

4-Chloro-N-cyclohexylaniline

The same procedure was carried out in the same manner as in Example 3 except that 4-chloroaniline was used instead of p-toluidine to obtain a white solid compound (71%).

$^1H$ NMR ($C_6D_6$): δ 0.77-0.85 (m, 2H, Cy), 1.01-1.17 (m, 3H, Cy), 1.45-1.56 (m, 3H, Cy), 1.76-1.79 (m, 2H, Cy), 2.85-2.90 (m, 1H, N—CH), 3.03 (br s, 1H, NH), 6.15 (d, J=8.8 Hz, 2H, $C_6H_4$), 7.09 (d, J=8.8 Hz, 2H, $C_6H_4$) ppm. $^{13}C$ {$^1H$} NMR ($C_6D_6$): δ 25.36, 26.34, 33.44, 51.70, 114.42, 121.31, 129.30, 146.21 ppm

Example 8

2-Bromo-4-chloro-N-cyclohexylaniline

The same procedure was carried out in the same manner as in Example 4 except that 4-chloro-N-cyclohexylaniline was used instead of N-cyclohexyl-4-methylaniline to obtain a colorless oil compound (90%).

$^1H$ NMR ($C_6D_6$): δ 0.82-0.93 (m, 2H, Cy), 0.96-0.98 (m, 1H, Cy), 1.00-1.11 (m, 2H, Cy), 1.37-1.41 (m, 1H, Cy), 1.36-1.41 (m, 2H, Cy), 1.66-1.69 (m, 2H, Cy), 2.79-2.90 (m, 1H, N—CH), 4.14 (brd, J=7.2 Hz, 1H, NH), 6.16 (d, J=8.8 Hz, 1H, $C_6H_3$), 6.98 (dd, J=2.8, 8.8 Hz, 1H, $C_6H_3$), 7.38 (d, J=2.8 Hz, 1H, $C_6H_3$) ppm. $^{13}C$ {$^1H$} NMR ($C_6D_6$): δ 25.06, 26.15, 33.03, 51.68, 109.87, 112.42, 121.04, 128.57, 132.16, 143.12 ppm

Example 9

N-Cyclohexyl-4-fluoroaniline

The same procedure was carried out in the same manner as in Example 3 except that 4-fluoroaniline was used instead of p-toluidine to obtain a brown oil compound (92%).

$^1H$ NMR ($C_6D_6$): δ 0.83-0.92 (m, 2H, Cy), 1.00-1.22 (m, 3H, Cy), 1.47-1.52 (m, 1H, Cy), 1.56-1.60 (m, 2H, Cy), 1.82-1.85 (m, 2H, Cy), 2.89-2.95 (m, 1H, N—CH), 3.00 (br s, 1H, NH), 6.22 (dd, J=4.4, 8.8 Hz, 2H, $C_6H_4$), 6.79 (t, J=8.8 Hz, 2H, $C_6H$) ppm. $^{13}C$ {$^1H$} NMR ($C_6D_6$): δ 25.45, 26.43, 33.64, 52.33, 114.13 (d, 3J=6.8 Hz, $C_6H_4F$), 155.78 (d, $^2J_{CF}$=22 Hz, $C_6H_4F$), 144.18 (d, $^4J_{CF}$=1.5 Hz, $C_6H_4F$—C), 155.66 (d, $^1J_{CF}$=231.3 Hz, $C_6H_4F$—C) ppm

Example 10

2-Bromo-N-cyclohexyl-4-fluoroaniline

The same procedure was carried out in the same manner as in Example 4 except that N-cyclohexyl-4-fluoroaniline was used instead of N-cyclohexyl-4-methylaniline to obtain a colorless oil compound (90%).

$^1H$ NMR ($C_6D_6$): δ 0.90-0.99 (m, 2H, Cy), 1.03-1.19 (m, 3H, Cy), 1.42-1.46 (m, 1H, Cy), 1.53-1.57 (m, 2H, Cy), 1.75-1.78 (m, 2H, Cy), 2.87-2.96 (m, 1H, N—CH), 3.97 (d, J=7.2 Hz, 1H, NH), 6.23 (dd, J=4.4, 8.8 Hz, 1H, $C_6H_3$), 6.72 (td, J=2.8, 8.8 Hz, 1H, $C_6H_3$), 7.09 (dd, J=2.8, 8.0 Hz, 1H, $C_6H_3$) ppm. $^{13}C$ {$^1H$} NMR($C_6D_6$): δ 25.20, 26.28, 33.29, 52.15, 109.14 (d, $^3J$=9.9 Hz, $C_6H_3$), 111.99 (d, $^3J_{CF}$=7.6 Hz, $C_6H_3$), 115.21 (d, $^2J_{CF}$=21.2 Hz, $C_6H_3$), 119.71 (d, $^2J_{CF}$=25 Hz, $C_6H_3$), 141.26 (d, $^4J_{CF}$=2.3 Hz, $C_6H_3$), 154.32 (d, $J_{CF}$=236 Hz, $C_6H_3$) ppm

Example 11

2-(2-Aminophenyl)-3,4-dimethyl-2-cyclopenten-1-one

Into a 100-mL Schlenk flask, 2-dihydroxyboryl-3-methyl-2-cyclopenten-1-one (1.27 g, 8.26 mmol), tetrakis(triphenylphosphine)palladium (0.182 g, 0.157 mmol) and sodium carbonate (1.25 g, 11.8 mmol) were put, and then degassed DME (21 mL) and distilled water (7 mL) purged with nitrogen gas were put thereto using a syringe. Then, to the flask, 2-bromo-N-cyclohexylaniline (2.00 g, 7.87 mmol) was put using a syringe, and was subject to reaction at 95° C. for 12 hours.

Thereafter, the reaction solution was transferred to a separatory funnel, and ethyl acetate (200 mL) and $H_2O$ (100 mL) were additionally added to the separatory funnel to extract an organic layer. The aqueous solution layer was further extracted from ethyl acetate (100 mL). Water was removed from the combined organic layer over $MgSO_4$, and filtered with a glass filter. The rotary evaporator was used to remove the remaining solvent, thereby obtaining a final product (1.23 g).

$^1$H NMR ($CDCl_3$): δ 1.13-1.28 (m, 4H, Cy), 1.32 (d, J=6.8 Hz, 3H, $CH_3$), 1.35-1.41 (m, 2H, Cy), 1.62-1.65 (m, 1H, Cy), 1.71-1.75 (m, 2H, Cy), 2.03 (s, 3H, $CH_3$), 1.98-2.07 (m, 1H, Cy), 2.19 (d, J=18.4 Hz, 1H, $CH_2$), 2.83 (dd, J=18.8, 6.8 Hz, 1H, $CH_2$), 2.95 (quintet, J=6.8 Hz, 1H, CH), 3.24-3.29 (m, 1H, N—CH), 3.48 (s, 1H, NH), 6.71 (t, J=8.8 Hz, 1H, $C_6H_4$), 6.74 (d, J=8.8 Hz, 1H, $C_6H_4$), 6.88 (d, J=8.8 Hz, 1H, $C_6H_4$), 7.20 (t, J=8.8 Hz, 1H, $C_6H_4$) ppm. $^{13}$C {$^1$H} NMR ($CDCl_3$): δ 16.31, 19.54, 24.82, 25.88, 33.13, 37.59, 43.52, 51.43, 111.34, 116.13, 117.19, 128.89, 129.44, 130.39, 144.72, 178.62, 206.65 ppm

Example 12

2-(2-Cyclohexylamino-4-methylphenyl)-3,4-dimethyl-2-cyclopenten-1-one

The same procedure was carried out in the same manner as in Example 11 except that 2-bromo-N-cyclohexyl-4-methylaniline was used instead of 2-bromo-N-cyclohexylaniline to obtain a yellow oil compound (98%).

$^1$H NMR ($C_6D_6$): δ 0.77 (d, J=6.8 Hz, 3H, $CH_3$), 1.10-1.22 (m, 4H, Cy), 1.42-1.48 (m, 2H, Cy), 1.54-1.62 (m, 2H, Cy), 1.63 (s, 3H, $CH_3$), 1.86 (dd, J=2.4, 18.4 Hz, 1H, $CH_2$), 1.96-2.06 (m, 2H, Cy), 2.18-2.23 (m, 1H, CH), 2.25 (s, 3H, $C_6H_3$—$CH_3$), 2.46 (dd, J=6.8, 18.4 Hz, 1H, $CH_2$), 3.14-3.24 (m, 1H, N—CH), 3.84 (br s, 1H, NH), 6.73 (d, J=8.4 Hz, 1H, $C_6H_3$), 6.86 (br s, 1H, $C_6H_3$), 7.08 (dd, J=2.4, 8.4 Hz, 1H, $C_6H_3$) ppm. $^{13}$C {$^1$H} NMR ($C_6D_6$): δ 16.19, 19.50, 20.81, 25.32, 26.53, 33.75, 37.67, 43.78, 52.02, 112.29, 119.07, 125.25, 129.85, 131.90, 139.93, 143.96, 176.77, 205.26 ppm

Example 13

2-(2-Cyclohexylamino-4-phenylphenyl)-3,4-dimethyl-2-cyclopenten-1-one

The same procedure was carried out in the same manner as in Example 11 except that 2-bromo-N-cyclohexyl-4-phenylaniline was used instead of 2-bromo-N-cyclohexylaniline to obtain a yellow oil compound (98%).

$^1$H NMR ($C_6D_6$): δ 0.75 (d, J=6.8 Hz, 3H, $CH_3$), 1.11-1.25 (m, 4H, Cy), 1.42-1.47 (m, 2H, Cy), 1.56-1.62 (m, 2H, Cy), 1.61 (s, 3H, $CH_3$), 1.87 (dd, J=2.0, 18.4 Hz, 1H, $CH_2$), 1.97-2.06 (m, 2H, Cy), 2.16-2.26 (m, 1H, CH), 2.46 (dd, J=6.4, 18.4 Hz, 1H, $CH_2$), 3.17-3.29 (m, 1H, N—CH), 4.14 (br s, 1H, NH), 6.79 (d, J=8.0 Hz, 1H, $C_6H_3$), 7.14 (tt, J=1.2, 7.2 Hz, 1H, $C_6H_5$), 7.27 (t, J=8.0 Hz, 2H, $C_6H_5$), 7.36 (d, J=2.0 Hz, 1H, $C_6H_3$), 7.55 (dd, J=2.0, 8.4 Hz, 1H, $C_6H_3$), 7.62 (dd, J=1.2, 8.0 Hz, 2H, $C_6H_5$) ppm. $^{13}$C {$^1$H} NMR ($C_6D_6$): δ 16.19, 19.39, 25.23, 26.45, 33.59, 37.80, 43.73, 51.81, 112.53, 119.36, 126.29, 126.76, 128.18, 129.02, 129.81, 130.25, 141.92, 145.76, 177.41, 205.30 ppm

Example 14

2-(4-Chloro-2-Cyclohexylaminophenyl)-3,4-dimethyl-2-cyclopenten-1-one

The same procedure was carried out in the same manner as in Example 11 except that 4-chloro-N-cyclohexylaniline was used instead of 2-bromo-N-cyclohexylaniline to obtain a yellow oil compound (97%).

$^1$H NMR ($C_6D_6$): δ 0.68 (d, J=7.2 Hz, 3H, $CH_3$), 1.03-1.17 (m, 4H, Cy), 1.40-1.46 (m, 2H, Cy), 1.47 (s, 3H, $CH_3$), 1.53-1.55 (m, 2H, Cy), 1.78 (dd, J=2.0, 18.4 Hz, 1H, $CH_2$), 1.84-1.94 (m, 2H, Cy), 2.08-2.12 (m, 1H, CH), 2.36 (dd, J=7.2, 18.4 Hz, 1H, $CH_2$), 2.97-3.08 (m, 1H, N—CH), 4.00 (br s, 1H, NH), 6.47 (d, J=8.8 Hz, 1H, $C_6H_3$), 7.01 (d, J=2.4 Hz, 1H, $C_6H_{21}$), 7.21 (dd, J=2.4, 8.8 Hz, 1H, $C_6H_3$) ppm. $^{13}$C {$^1$H} NMR ($C_6D_6$): δ 16.02, 19.30, 21.15, 26.37, 33.32, 37.80, 43.61, 51.76, 113.08, 120.46, 120.98, 129.05, 130.94, 138.63, 144.87, 178.02, 204.82 ppm

Example 15

2-(2-Cyclohexylamino-4-fluorophenyl)-3,4-dimethyl-2-cyclopenten-1-one

The same procedure was carried out in the same manner as in Example 11 except that N-cyclohexyl-4-fluoroaniline was used instead of 2-bromo-N-cyclohexylaniline to obtain a yellow oil compound (90%).

$^1$H NMR ($C_6D_6$): δ 0.76 (d, J=7.2 Hz, 3H, $CH_3$), 1.06-1.20 (m, 4H, Cy), 1.43-1.48 (m, 2H, Cy), 1.56 (s, 3H, $CH_3$), 1.54-1.62 (m, 2H, Cy), 1.81 (dd, J=2.0, 18.4 Hz, 1H, $CH_2$), 1.86-1.96 (m, 2H, Cy), 2.18-2.22 (m, 1H, CH), 2.40 (dd, J=6.8, 18.4 Hz, 1H, $CH_2$), 2.99-3.08 (m, 1H, N—CH), 3.78 (br s, 1H, NH), 6.48 (dd, J=4.8, 8.8 Hz, 1H, $C_6H_3$), 6.77 (dd, J=3.2, 8.8 Hz, 1H, $C_6H_3$), 6.91 (td, J=3.2, 8.8 Hz, 1H, $C_6H_3$) ppm. $^{13}$C {$^1$H} NMR ($C_6D_6$): δ 16.06, 19.30, 25.24, 26.45, 33.53, 37.77, 43.63, 52.21, 112.81 (d, $J_{CF}$=7.6 Hz, $C_6H_3$), 115.51 (d, $^2J_{CF}$=21.2 Hz, $C_6H_3$), 117.84 (d, $^2J_{CF}$=21.2 Hz, $C_6H_3$), 120.15 (d, $J_{CF}$=7.6 Hz, $C_6H_3$), 142.66, 154.01, 156.33, 177.80, 204.84 ppm

Example 16

2-(2,3,5-trimethylcyclopenta-1,4-dienyl)phenyl-N-cyclohexylamine

Into a 150-mL flask, $CeCl_3$ (5.27 g, 21.4 mmol) and THF (24 mL) were put, the temperature was lowered to −78° C., and then MeLi (1.6 M in diethyl ether, 13.4 mL, 21.4 mmol) was added to the mixture. If the color of the solution turned yellow, after 1 hour, 2-(2-aminophenyl)-3,4-dimethyl-2-cyclopenten-1-one (2.02 g, 7.13 mmol) was added to the flask, and the mixture was stirred for 2 hours at −78° C. Then, to the flask, distilled water (20 mL) and E.A (40 mL) were added to thereto, and the solution was transferred to a separatory funnel to extract an organic layer. Further, EA (10 mL) was further added to perform extraction twice, and the organic layer was combined. To the combined organic layer, an aqueous HCL solution (2 N, 20 mL) was added, and vigorously shaken for 2 minutes. The organic layer was neutralized with $NaHCO_3$ (4 mL), and then the organic layer was combined, and the remaining water was removed over $MgSO_4$. The glass filter was used to remove $CeCl_3$ and $MgSO_4$, and a rotary evaporator was used to remove the solvent. The remaining compound was separated by column chromatography (hexane:E.A=10:1) to obtain a pure final product (1.66 g, 83%).

$^1$H NMR ($CDCl_3$): δ 1.06-1.20 (m, 2H, Cy), 1.21-1.30 (m, 1H, Cy), 1.34-1.46 (m, 2H, Cy), 1.68 (d, J=1.2 Hz, 3H, $CH_3$), 1.74-1.81 (m, 3H, Cy), 1.87 (s, 3H, $CH_3$), 2.01 (s, 3H, $CH_3$), 2.03-2.10 (m, 2H, Cy), 2.94 (AB, J=22.8$H_Z$, 1H, $CH_3$), 3.01 (AB, J=22.8$H_Z$, 1H, $CH_2$), 3.29-3.34 (m, 1H, N—CH), 3.67 (br s, 1H, NH), 6.69 (td, J=1.2, 7.2 Hz, 1H, $C_6H_4$), 6.71 (d, J=8.0 Hz, 1H, $C_6H_4$), 6.93 (dd, J=1.6, 7.2 Hz, 1H, $C_6H_4$), 7.20 (ddd, J=1.6, 7.2, 8.0 Hz, 1H, $C_6H_4$) ppm. $^{13}$C {$^1$H} NMR ($CDCl_3$): δ 11.70, 13.73, 14.47, 25.13, 25.17, 26.05, 33.17, 33.50, 48.81, 51.50, 110.18, 115.50, 122.53, 127.76, 130.01, 133.11, 135.64, 136.80, 139.66, 144.86 ppm

Example 17

4-Methyl-2-(2,3,5-trimethylcyclopenta-1,4-dienyl)phenyl-N-cyclohexylamine

The same procedure was carried out in the same manner as in Example 16 except that 2-(2-cyclohexylamino-4-methylphenyl)-3,4-dimethyl-2-cyclopenten-1-one was used instead of 2-(2-aminophenyl)-3,4-dimethyl-2-cyclopenten-1-one to obtain a yellow solid compound (70%).

$^1$H NMR ($C_6D_6$): δ 0.92-1.04 (m, 3H, Cy), 1.12-1.22 (m, 2H, Cy), 1.40-1.48 (m, 1H, Cy), 1.50-1.57 (m, 2H, Cy), 1.81 (s, 3H, $CH_3$), 1.88 (s, 3H, $CH_3$), 1.90 (s, 3H, $CH_3$), 1.93-2.01 (m, 2H, Cy), 2.28 (s, 3H, $CH_3$), 2.72 (AB, J=22.8Hz, 1H, $CH_2$), 2.80 (AB, J=22.8Hz, 1H, $CH_3$), 3.16-3.25 (m, 1H, N—CH), 3.65 (br d, J=8.0 Hz, 1H, NH), 6.70 (d, J=8.0 Hz, 1H, $C_6H_3$), 6.93 (d, J=2.0 Hz, 1H, $C_6H_3$), 7.07 (dd, J=2.0, 8.0 Hz, 1H, $C_6H_3$) ppm

Example 18

4-Chloro-2-(2,3,5-trimethylcyclopenta-1,4-dienyl)phenyl-N-cyclohexylamine

The same procedure was carried out in the same manner as in Example 16 except that 2-(4-chloro-2-cyclohexylaminophenyl)-3,4-dimethyl-2-cyclopenten-1-one was used instead of 2-(2-aminophenyl)-3,4-dimethyl-2-cyclopenten-1-one to obtain a yellow oil compound (75%).

$^1$H NMR ($C_6D_6$): δ 0.87-1.04 (m, 3H, Cy), 1.11-1.23 (m, 2H, Cy), 1.41-1.47 (m, 1H, Cy), 1.50-1.58 (m, 2H, Cy), 1.80 (s, 3H, $CH_3$), 1.88 (s, 3H, $CH_3$), 1.90 (s, 3H, $CH_3$), 1.93-2.00 (m, 2H, Cy), 2.72 (AB, J=22.8Hz, 1H, $CH_2$), 2.80 (AB, J=22.8H, 1H, $CH_2$), 3.17-3.28 (m, 1H, N—CH), 3.86 (br d, J=8.0 Hz, 1H, NH), 6.77 (d, J=8.0 Hz, 1H, $C_6H_3$), 7.13 (t, J=8.0 Hz, 1H, $C_6H_5$), 7.27 (t, J=8.0 Hz, 2H, $C_6H_5$), 7.48 (d, J=2.4 Hz, H, $C_6H_3$), 7.59 (dd, J=2.4, 8.0 Hz, H, $C_6H_3$), 7.64 (d, J=8.0 Hz, 2H, $C_6H_5$) ppm. $^{13}$C {$^1$H} NMR ($C_6D_6$): δ 12.21, 13.90, 14.78, 25.42, 25.45, 26.35, 33.78, 33.81, 49.13, 51.67, 111.22, 123.43, 126.09, 126.60, 127.22, 128.98, 129.23, 129.35, 133.45, 136.29, 137.15, 140.73, 142.05, 145.00 ppm

Example 19

4-Fluoro-2-(2,3,5-trimethylcyclopenta-1,4-dienyl)phenyl-N-cyclohexylamine

The same procedure was carried out in the same manner as in Example 16 except that 2-(4-fluoro-2-cyclohexylaminophenyl)-3,4-dimethyl-2-cyclopenten-1-one was used instead of 2-(2-aminophenyl)-3,4-dimethyl-2-cyclopenten-1-one to obtain a yellow solid compound (60%).

$^1$H NMR ($C_6D_6$): δ 0.80-0.90 (m, 2H, Cy), 0.94-1.01 (m, 1H, Cy), 1.08-1.18 (m, 3H, Cy), 1.40-1.51 (m, 4H, Cy), 1.67 (s, 3H, $CH_3$), 1.77 (s, 3H, $CH_3$), 1.83 (s, 3H, $CH_3$), 2.61 (AB, J=22.8$H_Z$, 1H, $CH_2$), 2.71 (AB, J=22.8$H_Z$, 1H, $CH_2$), 2.99-3.07 (m, 1H, N—CH), 3.68 (br d, J=8.0 Hz, 1H, NH), 6.44 (d, J=8.8 Hz, 1H, $C_6H_3$), 7.07 (d, J=2.4 Hz, 1H, $C_6H_3$), 7.17 (dd, J=2.4, 8.8 Hz, 1H, $C_6H_3$) ppm, $^{13}$C {$^1$H} NMR ($C_6D_6$): δ 11.93, 13.82, 14.54, 25.36, 25.39, 26.29, 33.56, 33.59, 49.10, 51.65, 111.77, 120.79, 124.66, 128.24, 130.18, 133.70, 135.67, 137.73, 139.52, 144.15 ppm

Example 20

Phenylene (N-cyclohexylamido)(2,3,5-trimethylcyclopentadienyl)titanium dichloride To a 25-mL flask, 2-(2,3,5-trimethylcyclopenta-1,4-dienyl)phenyl-N-cyclohexylamine (0.196 g, 0.696 mmol) and $Ti(N(Me)_2)_4$ (0.156 g, 0.696 mmol), which had been diluted with toluene (2 mL), were put. The solution was subject to reaction for 2 days under heating to 80° C., and then the solvent was removed to obtain a red solid. To the obtained solid, toluene (2 mL) and $Me_2SiCl_2$ (0.269 g, 2.09 mmol) was successively added at normal temperature, and stirred for 4 hours at normal temperature, and then the solvent was removed. Then, the solid was recrystallized from hexane at −30° C. to obtain a red solid as a final product (0.183 g, 66%).

$^1$H NMR($C_6D_6$): δ 0.83-1.00 (m, 2H, Cy), 1.35-1.51 (m, 3H, Cy), 1.64 (s, 3H, $CH_3$), 1.66-1.74 (m, 3H, Cy), 1.75 (s, 3H, $CH_3$), 1.81-1.95 (m, 2H, Cy), 2.09 (s, 3H, $CH_3$), 5.46-5.58 (m, 1H, N—CH), 6.06 (s, 1H, Cp-H), 6.65 (d, J=7.2 Hz, 1H, $C_6H_4$), 6.95 (td, J=0.8, 7.2 Hz, 1H, $C_6H_4$), 7.07 (dd, J=2.0, 7.2 Hz, 1H, $C_6H_4$), 7.11 (td, J=2.0, 7.2 Hz, 1H, $C_6H_4$) ppm. $^{13}$C {$^1$H} NMR ($C_6D_6$): δ 12.38, 14.48, 14.82, 25.81, 27.08, 27.51, 59.57, 111.11, 118.50, 123.05, 128.49, 128.99, 131.56, 132.17, 142.13, 142.93, 143.42, 164.02 ppm. Anal. Calc. ($C_{20}H_{25}Cl_2NTi$): C, 60.33; H, 6.33; N, 3.52%. Found: C, 60.19; H, 6.52; N, 3.29%.

Example 21

4-Methylphenylene (N-cyclohexylamido)(2,3,5-trimethylcyclopentadienyl)titanium dichloride The same procedure was carried out in the same manner as in Example 20 except that 4-methyl-2-(2,3,5-trimethylcyclopenta-1,4-dienyl)phenyl-N-cyclohexylamine was used instead of 2-(2,3,5-trimethylcyclopenta-1,4-dienyl)phenyl-N-cyclohexylamine to obtain a red solid compound (59%).

$^1$H NMR ($C_6D_6$): δ 0.84-1.00 (m, 2H, Cy), 1.37-1.53 (m, 3H, Cy), 1.69 (s, 3H, $CH_3$), 1.71-1.76 (m, 2H, Cy), 1.80 (s, 3H, $CH_3$), 1.85-1.97 (m, 2H, Cy), 2.10-2.18 (m, 1H, Cy), 2.11 (s, 3H, $CH_3$), 2.21 (s, 3H, $CH_3$), 5.57 (m, 1H, N—CH), 6.09 (s, 1H, Cp-H), 6.60 (d, J=8.4 Hz, 1H, $C_6H_3$), 6.91 (s, 1H, $C_6H_3$), 6.94 (d, J=8.4 Hz, 1H, $C_6H_3$) ppm. $^{13}$C {$^1$H} NMR ($C_6D_6$): δ 12.45, 14.50, 14.89, 20.69, 25.85, 27.10, 27.58, 59.59, 110.77, 118.38, 128.87, 129.68, 131.37, 132.55, 132.75, 142.06, 142.64, 143.11, 161.82 ppm. Anal. Calc. ($C_{21}H_{27}Cl_2NTi$): C, 61.19; H, 6.60; N, 3.40%. Found: C, 60.94; H, 6.54; N, 3.61%.

Example 22

4-Phenylphenylene (N-cyclohexylamido)(2,3,5-trimethylcyclopentadienyl)titanium dichloride The same procedure was carried out in the same manner as in Example 20 except that 4-phenyl-2-(2,3,5-trimethylcyclopenta-1,4-dienyl)phenyl-N-cyclohexylamine was used instead of 2-(2,3,5-trimethylcyclopenta-1,4-dienyl)phenyl-N-cyclohexylamine to obtain a red solid compound (87%).

$^1$H NMR ($C_6D_6$): δ 0.93-1.06 (m, 2H, Cy), 1.38-1.56 (m, 4H, Cy), 1.70 (s, 3H, $CH_3$), 1.72-1.80 (m, 2H, Cy), 1.81 (s, 3H, $CH_3$), 1.88-2.03 (m, 2H, Cy), 2.13 (s, 3H, $CH_3$), 5.54 (m, 1H, N—CH), 6.10 (s, 1H, Cp-H), 6.71 (d, J=8.0 Hz, 1H, $C_6H_3$), 7.20 (d, J=8.0 Hz, 1H, $C_6H_5$), 7.31 (t, J=8.0 Hz, 2H, $C_6H_5$), 7.38 (d, J=2.0 Hz, 1H, $C_6H_3$), 7.44 (dd, J=2.0, 8.0 Hz, 1H, $C_6H_3$), 7.58 (dd, J=2.0, 8.0 Hz, 2H, $C_6H_5$) ppm. $^{13}$C {$^1$H} NMR ($C_6D_6$): δ 12.58, 14.63, 15.03, 25.95, 27.17, 27.68, 59.73, 111.22, 118.40, 126.81, 126.99, 127.27, 128.79, 129.05, 131.50, 132.68, 136.14, 140.46, 141.77, 142.72, 143.20, 163.14 ppm. Anal. Calc. ($C_{26}H_{29}Cl_2NTi$): C, 65.84; H, 6.16; N, 2.95%. Found: C, 65.92; H, 6.05; N, 3.13%.

Example 23

4-Chlorophenylene (N-cyclohexylamido)(2,3,5-trimethylcyclopentadienyl) titanium dichloride The same procedure was carried out in the same manner as in Example 20 except that 4-chloro-2-(2,3,5-trimethylcyclopenta-1,4-dienyl)phenyl-N-cyclohexylamine was used instead of 2-(2,3,5-trimethylcyclopenta-1,4-dienyl)phenyl-N-cyclohexylamine to obtain a red solid compound (73%).

$^1$H NMR ($C_6D_6$): δ 0.82-0.96 (m, 2H, Cy), 1.31-1.50 (m, 4H, Cy), 1.56 (s, 3H, $CH_3$), 1.67 (s, 3H, $CH_3$), 1.68-1.78 (m, 2H, Cy), 1.91-2.03 (m, 2H, Cy), 2.04 (s, 3H, $CH_3$), 5.39 (m, 1H, N—CH), 6.00 (s, 1H, Cp-H), 6.40 (d, J=8.8 Hz, 1H, $C_6H_3$), 7.04 (d, J=2.8 Hz, 1H, $C_6H_3$), 7.10 (dd, J=2.8, 8.8 Hz, 1H, $C_6H_3$) ppm. $^{13}$C {$^1$H} NMR ($C_6D_6$): δ 12.30, 14.44, 14.74, 25.72, 26.97, 27.28, 59.67, 111.71, 118.64, 128.33, 128.45, 129.05, 131.85, 133.38, 140.29, 142.78, 143.28, 162.54 ppm. Anal. Calc. ($C_{20}H_{24}Cl_3NTi$): C, 55.52; H, 5.59; N, 3.24%. Found: C, 55.38; H, 5.79; N, 3.34%

Example 24

4-Fluorophenylene (N-cyclohexylamido)(2,3,5-trimethylcyclopentadienyl) titanium dichloride The same procedure was carried out in the same manner as in Example 20 except that 4-fluoro-2-(2,3,5-trimethylcyclopenta-1,4-dienyl)phenyl-N-cyclohexylamine was used instead of 2-(2,3,5-trimethylcyclopenta-1,4-dienyl)phenyl-N-cyclohexylamine to obtain a red solid compound (90%).

$^1$H NMR ($C_6D_6$): δ 0.88-1.03 (m, 2H, Cy), 1.32-1.47 (m, 2H, Cy), 1.47-1.56 (m, 1H, Cy), 1.61 (s, 3H, $CH_3$), 1.71 (s, 3H, $CH_3$), 1.72-1.84 (m, 3H, Cy), 1.93-2.05 (m, 2H, Cy), 2.09 (s, 3H, $CH_3$), 5.38-5.47 (m, 1H, N—CH), 6.05 (s, 1H, Cp-H), 6.43 (dd, J=4.8, 8.8 Hz, 1H, $C_6H_3$), 6.79-6.85 (m, 2H, $C_6H_3$) ppm. $^{13}$C {$^1$H} NMR($C_6D_6$): δ 12.61, 14.75, 15.04, 26.03, 27.29, 27.58, 27.66, 59.74, 111.38 (d, 3 J=8.3 Hz, $C_6H_3$), 114.80 (d, $^2J_{CF}$=22.8 Hz, $C_6H_3$), 116.49 (d, $^2J_{CF}$=23.5 Hz, $C_6H_3$), 118.62, 131.69, 133.42 (d, $^3J_{CF}$=8.3 Hz, $C_6H_3$), 140.02, 142.53, 143.00, 159.74 (d, $^1J_{CF}$=240.4 Hz, $C_6H_3$), 160.02 ppm. $^{19}$F NMR ($C_6D_6$): δ-28.83 (dd, J=7.8, 12.4 Hz) ppm.

Example 25

4-(4-(cyclohexylamino)benzyl)-N-cyclohexylbenzeneamine

To a 250-mL flask, 4,4-methyleneaniline (4.000 g, 20.175 mmol), cyclohexanone (15.839 g, 161.396 mmol), molecular sieves (4 Å, 10.0 g) and toluene (30 mL) as a solvent were put. The solution was subject to reaction at 100° C. for 2 days. After reaction, the solution was cooled to room temperature, the molecular sieves were filtered out, and dried in vacuo at 60° C. to obtain 4-(4-(cyclohexylideneamino)benzyl)-N-cyclohexylbenzeneamine. The obtained compound was dissolved in methanol (60 mL), sodium borohydride (4.576 g, 121.047 mmol) was added thereto, and the mixture was reacted at room temperature for 2 hours. Thereafter, the reaction solution was neutralized with a 1 N KOH (80 mL) solution. The neutralized solution was transferred to a separatory funnel and the organic layer was extracted from M.C. (methylenechloride) (60 mL) twice. The combined organic layer was dried over $MgSO_4$, and then recrystallized from hexane and ethyl acetate solvent (v/v=20:1) to obtain a white solid compound (3.765 g, 51%).

$^1$H NMR ($CDCl_3$): 6.94 (d, 4H, Ph),Ph), 3.72 (s, 2H, $CH_2$), 3.37 (s, 2H, NH), 3.19 (m, 2H, $CH_2^{Cy}$), 2.02 (m, 4H, $CH_2^{Cy}$), 1.72 (m, 4H, $CH_2^{Cy}$), 1.57 (m, 2H, $CH_2^{Cy}$), 1.33 (m, 4H, $CH_2^{Cy}$), 1.21 (m, 2H, $CH_2^{Cy}$) 1.12 (m, 4H, $CH_2^{Cy}$)

Example 26

4-(3-Bromo-4-(cyclohexylamino)benzyl)-2-bromo-N-cyclohexylbenzeneamine

In a 100-mL flask, 4-(4-(cyclohexylamino)benzyl)-N-cyclohexylbenzeneamine (1.5 g, 4.137 mmol) was dissolved in M.C. (15 μL), and the solution was cooled to 0° C. To the flask, a $Br_2$ (1.322 mL, 8.275 mmol) solution in M.C. (10 mL) was slowly added at 0° C. for 30 minutes and subject to reaction for 2 hours. Thereafter, the reaction solution was neutralized with a 1 N KOH (10 mL) solution. The neutralized solution was transferred to a separatory funnel and the organic layer was extracted from M.C. (40 μL) twice. The combined organic layer was dried over $MgSO_4$, and then purified by column chromatography using hexane and ethyl acetate solvent (v/v=20:1) to obtain a white solid compound (1.523 g, 71%).

$^1$H NMR ($C_6D_6$): 7.35 (d, 2H, Ph), 6.89 (dd, 2H, Ph), 6.45 (d, 2H, Ph), 4.22 (d, 2H, NH), 3.54 (s, 2H, $CH_2$), 3.04 (m, 2H, $CH^{Cy}$), 1.80 (m, 4H, $CH^{Cy}$), 1.52 (m, 4H, $CH^{Cy}$), 1.41 (m, 2H, $CH^{Cy}$), 1.16-0.93 (m, 10H, $CH^{Cy}$). $^{13}$C NMR($C_6D_6$): 142.74, 133.04, 130.86, 129.14, 112.29, 110.28, 51.81, 39.78, 33.31, 26.25, 25.17

Example 27

4-(3-(3,4-Dimethylcyclopenta-1,3-dienone)-4-(cyclohexylamino)benzyl)-2-(3,4-dimethylcyclopenta-1,3-dienone)-N-cyclohexylbenzeneamine Boronic acid (0.857 g, 5.565 mmol), $Na_2CO_3$ (0.843 g, 7.951 mmol), $Pd(P(Ph)_3)_4$ (0.123 g, 0.106 mmol) and the compound prepared in Example 26 (1.378 g, 2.650 mmol) were dissolved in DME (12 mL) and water (4 mL), and the solution was subject to reaction at 95° C. for 40 hours. The reaction solution was cooled to room temperature, and then the organic layer was extracted from ethyl acetate (30 mL). The obtained, extracted solution was dried over $MgSO_4$, and then purified by column chromatography using hexane and ethyl acetate (3:1) solvent to obtain a yellow solid compound (1.206 g, 79%).

$^1$H NMR ($CDCl_3$): 6.96 (dd, 2H, Ph), 6.64 (d, 2H, Ph), 6.60 (d, 2H, Ph), 3.73 (s, 2H, $CH_2$), 3.32 (s, 2H, NH), 3.19 (m, 2H, $CH^{Cy}$), 2.87 (m, 2H, CH), 2.74 (dd, 2H, $CH_2$), 2.11 (dd, 2H, $CH_2$), 1.95 (m, 4H, $CH_2^{Cy}$), 1.93 (s, 6H, Me), 1.67 (m, 4H, $CH_2^{Cy}$), 1.57 (m, 2H, $CH_2^{Cy}$), 1.36-1.03 (m, 10H, $CH_2^{Cy}$), 1.25 (d, 6H, Me).

Example 28

4-(3-(2,3,5-Trimethylcyclopenta-1,3-diene)-4-(cyclohexylamino)benzyl)-2-(2,3,5-trimethylcyclopenta-1,3-diene)-N-cyclohexylbenzeneamine Anhydrous $CeCl_3$ (3.744 g, 15.203 mmol) was dissolved in THF (30 mL), and the solution was cooled to −78° C. To the solution, MeLi (9.502 mL, 15.203 mmol) was slowly added, and then subject to reaction at −78° C. for 1 hour. The compound (4-(3-(3,4-dimethylcyclopenta-1,3-dienone)-4-(cyclohexylamino)benzyl)-2-(3,4-dimethylcyclopenta-1,3-dienone)-N-cyclohexylbenzeneamine) (1.100 g, 1.900 mmol) was added thereto, and then further subject to reaction at −78° C. for 2 hours. To the solution, distilled water (30 mL) and ethyl acetate (40 μL) were added to extract the organic layer. To the extracted organic layer, 2 N HCl was added, and subject to reaction for 2 minutes. The resultant was neutralized with a $NaHCO_3$ base, and the obtained organic layer was dried over $MgSO_4$. The obtained oil was purified by column chromatography using hexane and ethyl acetate (v/v, 20:1) solvent to obtain a white oil (0.502 g, 46%).

$^1$H NMR ($CDCl_3$): 6.95 (dd, 2H, Ph), 6.70 (d, 2H, Ph), 6.55 (d, 2H, Ph), 3.74 (s, 2H, $CH_2$), 3.43 (d, 2H, NH), 3.20 (m, 2H, $CH^{Cy}$), 2.86 (qd, 4H, $CH_2$), 1.96 (m, 4H, $CH_2^{Cy}$) 1.91 (s, 6H, Me), 1.76 (s, 6H, Me), 1.70-1.54 (m, 6H, $CH_2^{Cy}$), 1.54 (s, 6H, Me), 1.30 (m, 4H, $CH_2^{Cy}$), 1.16 (m, 2H, $CH_2^{Cy}$), 1.01 (m, 4H, $CH_2CH_2^{Cy}$).

Example 29

Methylidene-bis-(3,4-phenylene(cyclohexylamido)(2,3,5-Trimethylcyclopentadienyl)titanium dichloride A solution containing 4-(3-(2,3,5-trimethylcyclopenta-1,3-diene)-4-(cyclohexylamino)benzyl)-2-(2,3,5-trimethylcyclopenta-1,3-diene)-N-cyclohexylbenzeneamine (1.1481 g, 2.58 mmol), $Ti(N(Me_2))_4$ (1.271 g, 5.67 mmol) and toluene (15 mL) was subject to reaction at 80° C. for 2 days. Then, the solvent was removed from the solution, and the resultant was extracted from pentane to obtain a red solid. The solid compound was dissolved in toluene (15 mL), and $Me_2SiCl_2$ (1.996 g, 15.46 mmol) was added to the solution. Then, the solution was stirred at normal temperature for 4 hours, and the solvent was removed therefrom. To the resultant, pentane was added and the mixture was pulverized and filtered to obtain a red solid compound (1.808 g, overall 87%).

$^1$H NMR($C_6D_6$): δ 0.91-0.97 (m, 2H, Cy-$CH_3$), 1.40-1.52 (m, 6H, Cy-$CH_2$), 1.68-1.75 (m, 3H, Cy-$CH_3$), 1.70 (s, 6H, $CH_3$), 1.82 (s, 6H, $CH_3$), 1.89-2.00 (m, 6H, Cy-$CH_3$), 2.06-2.18 (m, 3H, Cy-$CH_3$), 2.13 (s, 6H, $CH_3$), 3.95 (s, 2H, bridged-$CH_3$), 5.50-5.61 (m, 2H, N—CH), 6.10 (s, 2H, Cp-H), 6.68 (d, J=8.0 Hz, 2H, $C_6H_3$—CH), 7.04 (s, 2H, $C_6H_3$—CH), 7.09 (d, J=8.0 Hz, 2H, $C_6H_3$—CH) ppm, $^{13}C\{^1H\}$ NMR($C_6D_6$): δ 12.76, 44.80, 15.17, 26.09, 27.36, 27.88, 27.95, 59.87, 110.94, 118.52, 128.87, 129.53, 131.59, 132.76, 136.41, 141.80, 142.57, 143.03, 162.45 ppm.

Example 30

4-(3-(2,3,5-trimethylcyclopentadienyl)-4-(cyclohexylamido)benzyl)-2-(2,3,5-tri-methylcyclopentadienyl)-N-cyclohexylbenzeneamido tetralithium salt The compound 4-(3-(2,3,5-trimethylcyclopenta-1,3-diene)-4-(cyclohexylamino)benzyl)-2-(2,3,5-trimethylcyclopenta-1,3-diene)-N-cyclohexylbenzeneamine (0.390 g, 0.68 mmol) prepared in Example 28 was dissolved in cold diethyl ether (4 mL, −30° C.) as a solvent, n-BuLi (1.140 mL, 2.85 mmol, 2.5 M in hexane) was slowly added thereto, and then the mixture was subject to reaction for 12 hours. The pale yellow precipitate was filtered, and washed with pentane (12 mL) to obtain a white solid (yield: 100%). $^1$H and $^{13}$C NMR spectrum showed that a tetralithium salt compound was clearly produced, and 0.58 diethyl ether existed.

$^1$H NMR($C_6D_6$+$^d$Py): δ 1.14-1.26 (m, 6H, Cy-$CH_2$), 1.36-1.51 (m, 4H, Cy-$CH_2$), 1.54-1.62 (m, 4H, Cy-$CH_2$), 1.63-1.74 (m, 6H, Cy-$CH_2$), 1.90 (s, 6H, $CH_3$), 2.14 (s, 6H, $CH_3$), 2.38 (s, 6H, $CH_3$), 3.37-3.44 (m, 2H, N—CH), 4.23 (s, 2H, bridged-$CH_2$), 5.86 (s, 2H, Cp-H), 6.61 (d, J=5.6 Hz, 2H, $C_6H_3$—CH), 7.36 (br s, 2H, $C_6H_3$—CH), 7.46 (s, 2H, $C_6H_3$—CH) ppm.

Example 31

Methylidene-bis(3,4-phenylene(cyclohexylamido)(2,3,5-trimethylcyclopentadienyl)-titanium dimethyl)

$TiCl_4$ DME (0.644 g, 2.30 mmol) was dissolved in diethyl ether (16 mL) solvent, and the solution was stored at −30° C. for 30 minutes. To this solution, MeLi (2.106 g, 4.60 mmol, 1.6 M in diethyl ether w/o LiBr) was slowly added for 15 minutes. To the reaction solution, the compound 4-(3-(2,3,5-trimethylcyclopentadienyl)-4-(cyclohexylamido)benzyl)-2-(2,3,5-trimethyl cyclopentadienyl)-N-cyclohexylbenzeneamido tetralithium salt (0.800 g, 1.15 mmol) prepared in Example 30 was added, and the mixture was subject to reaction at room temperature for 3 hours. All of the solvents were dried in vacuo, and extracted from pentane (25 mL) to obtain a dark red oil (0.670 g, 88%).

$^1$H NMR($C_6D_6$): δ 0.47 (br s, 6H, Ti—$CH_3$), 0.61 (br s, 6H, Ti—$CH_3$), 1.03-1.17 (m, 2H, Cy-$CH_2$), 1.40-1.53 (m, 3H, Cy-$CH_2$), 1.56 (s, 6H, $CH_3$), 1.67 (s, 6H, $CH_3$), 1.80-1.88 (m, 6H, Cy-$CH_2$), 1.90-2.04 (m, 3H, Cy-$CH_2$), 2.13 (s, 6H, $CH_2$), 2.27-2.39 (m, 6H, Cy-$CH_2$), 3.95 (s, 2H, bridged-$CH_2$), 5.89 (br s, 2H, N—CH), 6.10 (s, 2H, Cp-H), 6.70 (br s, 2H, $C_6H_3$—CH), 7.07 (s, 2H, $C_6H_3$—CH), 7.12 (d, J=5.6 Hz, 2H, $C_6H_3$—CH) ppm, $^{13}C\{^1H\}$ NMR($C_6D_6$): δ 11.82, 13.89, 14.13, 26.39, 27.96, 30.63, 41.07, 44.25, 47.91, 56.48, 108.37, 110.66, 112.85, 122.12, 129.93, 132.12, 133.42, 135.68, 136.30, 160.25 ppm.

The invention claimed is:

1. A compound of the following ormula 3:

[Formula 3]

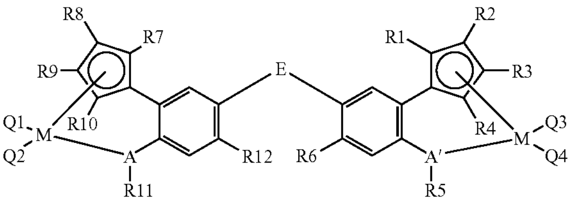

wherein

R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;

R5 and R11 are each independently an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom;

E is a covalent bridging group for bridging two phenylene rings, which is an epoxy group; an epithio group; a carbonyl group; a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms;

Q1 to Q4 are each independently a halogen radical; an alkylamido radical having 1 to 20 carbon atoms; an arylamido radical; an alkyl radical having 1 to 20 carbon atoms; an alkenyl radical; an aryl radical; an alkylaryl radical; an arylalkyl radical; or an alkylidene radical having 1 to 20 carbon atoms; and M is a Group 4 transition metal.

2. The compound according to claim 1, wherein R1, R4, R7 and R10; R2, R3, R8 and R9; R6 and R12; and R5 and R11 are the same to each other.

3. The compound according to claim 1, wherein the formula 3 is represented by the following formula 4:

[Formula 4]

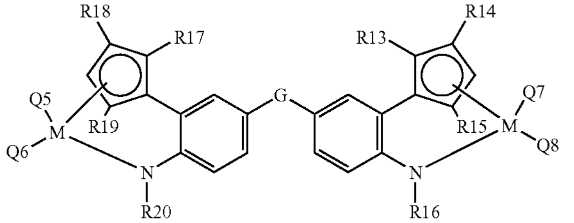

wherein

R13 to R15, and R17 to R19 are each independently a hydrogen atom; or an alkyl radical having 1 to 20 carbon atoms; an aryl radical; or a silyl radical;

R16 and R20 are each independently an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; or an arylalkyl radical;

Q5 to Q8 are each independently a halogen radical; an alkylamido radical having 1 to 20 carbon atoms; an arylamido radical; or an alkyl radical having 1 to 20 carbon atoms;

G is an epoxy group; an epithio group; a carbonyl group; a heterohydrocarbylene group having 1 to 60 carbon atoms, substituted with a substituent containing an oxygen or nitrogen atom; or —C(R21)$_2$—, wherein R21 is hydrogen, or alkyl having 1 to 20 carbon atoms; aryl; silyl; alkenyl having 2 to 20 carbon atoms; alkylaryl; or arylalkyl; and M is a Group 4 transition metal.

4. The compound according to claim 3, wherein the formula 4 is represented by the following formula 5:

[Formula 5]

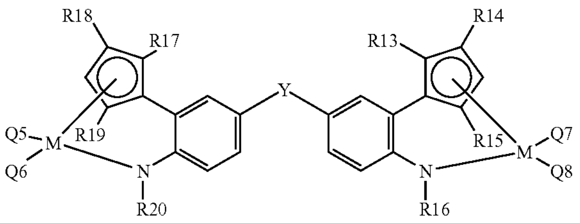

wherein

Y is —CH$_2$—, —C(CH$_3$)$_2$—, or —C(=O)—; and

R13 to R20, Q5 to Q8, and M each have the same meanings as defined in the formula 4.

5. The compound according to claim 1, wherein the formula 3 is represented by the following formula 6:

[Formula 6]

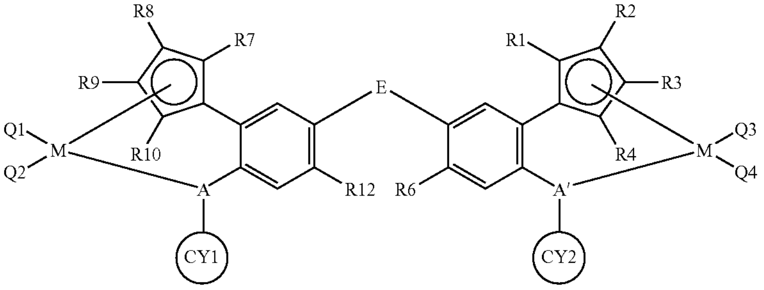

wherein

R1 to R4, R6 to R10, R12, Q1 to Q4, A, A', E and M each have the same meanings as defined in the formula 3, and CY1 and CY2 are each independently an aliphatic ring having 5 to 20 carbon atoms.

6. The compound according to claim 5, wherein the formula 6 is represented by the following formula 7:

[Formula 7]

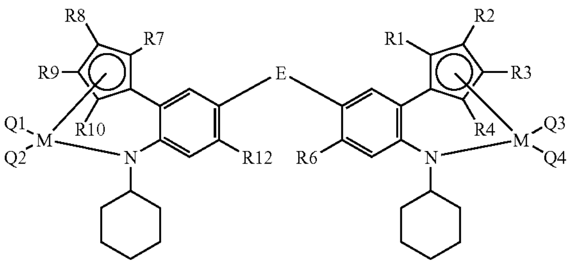

wherein R1 to R4, R6 to R10, R12, Q1 to Q4, E and M each have the same meanings as defined in the formula 6.

7. A compound of the following formula 10:

[Formula 10]

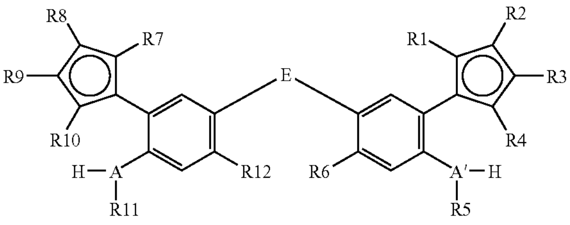

wherein

R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;

R5 and R11 are each independently an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom; and

E is a covalent bridging group for bridging two phenylene rings, which is an epoxy group; an epithio group; a carbonyl group; a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms.

8. A compound of the following formula 11:

[Formula 11]

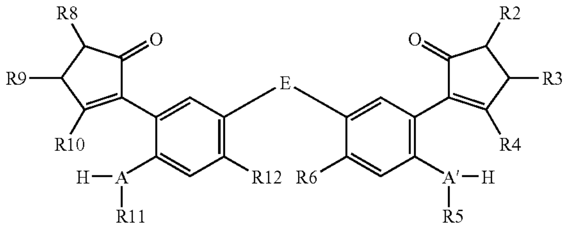

wherein

R2 to R4, and R8 to R10 are each in dependently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R2 to R4, and R8 to R10 may be bonded together by an alkylidene radical containing an aryl or alkyl radical having 1 to 20 carbon atoms to form a ring;

R5 and R11 are each independently an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom; and

E is a covalent bridging group for bridging two phenylene rings, which is an epoxy group; an epithio group; a carbonyl group; a silane group; a disilane group; a substituted or unsubstituted hydrocarbylene group having 1 to 60 carbon atoms; or a substituted or unsubstituted, Group 4B, 5B or 6B element-containing hydrocarbylene group having 1 to 60 carbon atoms.

9. A compound of the following formula 12:

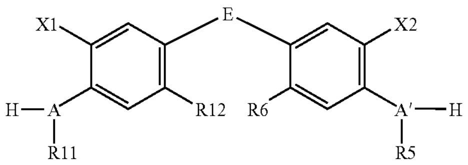

wherein

R5 and R11 are each independently alkyl having 1 to 20 carbon atoms; cycloalkyl having 3 to 20 carbon atoms; aryl; silyl; alkenyl having 2 to 20 carbon atoms; alkylaryl; arylalkyl; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom;

E is a covalent bridging group for bridging two phenylene rings, which is an epoxy group; an epithio group; a carbonyl group; a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms; and X1 and X2 are independently a halogen atom.

10. A method for preparing a binuclear transition metal compound, comprising the steps of:

a) reacting a compound represented by the following formula 17 with a organic compound represented by the formula 13 to prepare a compound represented by the following formula 12;

b) reacting the compound represented by the following formula 12 with a boronic acid compound represented by the following formula 14 to prepare a compound represented by the following formula 11;

c) reacting the compound represented by the formula 11 with an R'Li or R'MgX compound, and then adding an acid thereto to prepare a compound represented by the formula 10, wherein R' is a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; and X is a halogen atom;

d) reacting the compound represented by the formula 10 with a base to prepare a dilithium compound represented by the following formula 18; and e) reacting the dilithium compound represented by the formula 18 with an in-situ mixture of alkyllithium and $MX_4$ (wherein X=halogen; and N is a Group 4 transition metal) to prepare a compound represented by the following formula 3:

[Formula 3]

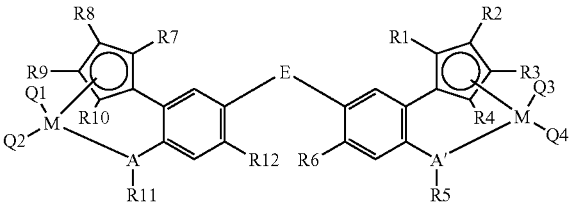

wherein

R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;

R5 and R11 are each independently an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom;

E is a covalent bridging group for bridging two phenylene rings and is an epoxy group; an epithio group; a carbonyl group; a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms;

Q1 to Q4 are each independently a halogen radical; an alkylamido radical having 1 to 20 carbon atoms; an arylamido radical; an alkyl radical having 1 to 20 carbon atoms; an alkenyl radical; an aryl radical; an alkylaryl radical; an arylalkyl radical; or an alkylidene radical having 1 to 20 carbon atoms; and N is a Group 4 transition metal;

[Formula 10]

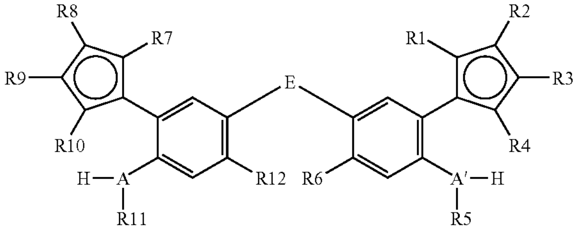

wherein R1 to R12, A, A' and E each have the same meanings as defined in the formula 3;

[Formula 11]

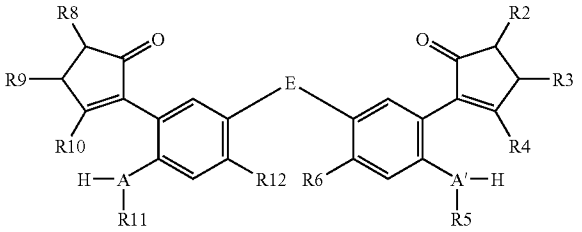

wherein R2 to R6 and R8 to R12, A, A' and E each have the same meanings as defined in the formula 3;

[Formula 12]

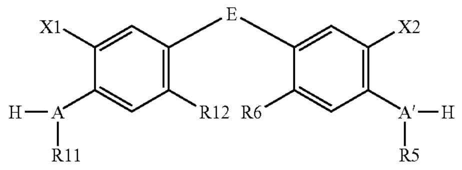

wherein R5, R6, R11, R12, A, A' and E each have the same meanings as defined in the formula 3, and, X1 and X2 are each independently a halogen atom;

[Formula 13]

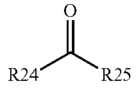

wherein

R24 and R25 are each independently an aryl or alkyl radical having 1 to 20 carbon atoms, and R24 and R25 may be bonded to each other;

[Formula 14]

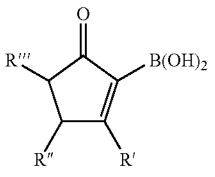

wherein

R', R'' and R''' are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; and

[Formula 17]

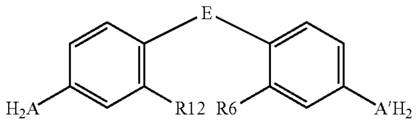

wherein R6 to R12, A, A' and E each have the same meanings as defined in the formula 3;

[Formula 18]

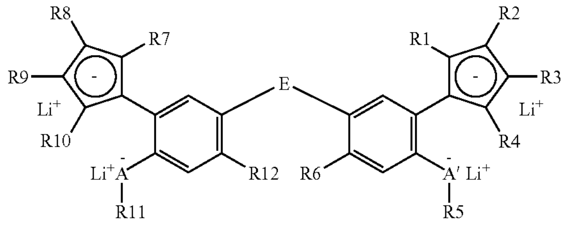

wherein R1 to R12, A, A' and E each have the same meanings as defined in the formula 3.

11. A method for preparing a binuclear transition metal compound, comprising the steps of:

a) reacting a compound represented by the following formula 17 with a organic compound represented by the following formula 13 to prepare a compound represented by the following formula 12;

b) reacting the compound represented by the formula 12, and a boronic acid compound represented by the formula 14 to prepare a compound represented by the following formula 11;

c) reacting the compound represented by the formula 11 with an R'Li or R'MgX compound, and then adding an acid thereto to prepare a compound represented by the formula 10, wherein R' is a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; and X is a halogen atom; and d') reacting the compound represented by the formula 10 with a metal compound represented by the following formula 16, and then adding a $(CH_3)_nSiX_{4-n}$ (wherein X=a halogen atom; and n=0, 1, 2 or 3) compound thereto to prepare a compound represented by the formula 3:

[Formula 3]

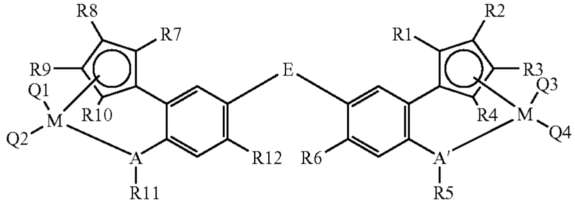

wherein

R1 to R4, and R7 to R10 are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; at least two of R1 to R4, and R7 to R10 may be bonded together by an alkylidene radical containing an aryl or alkyl radical having 1 to 20 carbon atoms to form a ring;

R5 and R11 are each independently an alkyl radical having 1 to 20 carbon atoms; a cycloalkyl radical having 3 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl;

R6 and R12 are each independently a hydrogen atom; a halogen radical; an alkyl radical having 1 to 20 carbon atoms; or an aryl radical, or R6 and R12 may be bonded to each other;

A and A' are each independently a nitrogen or phosphorous atom;

E is a covalent bridging group for bridging two phenylene rings and is an epoxy group; an epithio group; a carbonyl group; a silane group; a disilane group; a substituted or unsubstituted hydrocarbylene group having 1 to 60 carbon atoms; or a substituted or unsubstituted, Group 4B, 5B or 6B element-containing heterohydrocarbylene group having 1 to 60 carbon atoms;

Q1 to Q4 are each independently a halogen radical; an alkylamido radical having 1 to 20 carbon atoms; an arylamido radical; an alkyl radical having 1 to 20 carbon atoms; an alkenyl radical; an aryl radical; an alkylaryl radical; an arylalkyl radical; or an alkylidene radical having 1 to 20 carbon atoms; and M is a Group 4 transition metal;

[Formula 10]

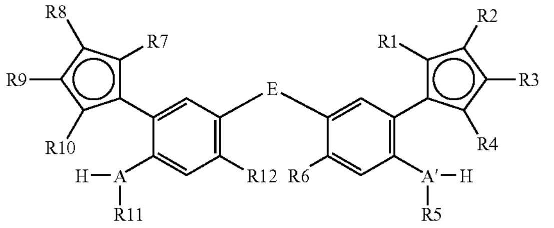

wherein R1 to R12, A, A' and E each have the same meanings as defined in the formula 3;

[Formula 11]

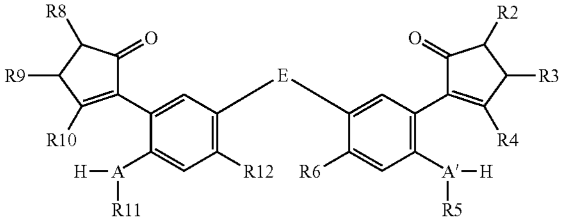

wherein R2 to R6 and R8 to R12, A, A' and E each have the same meanings as defined in the formula 3;

[Formula 12]

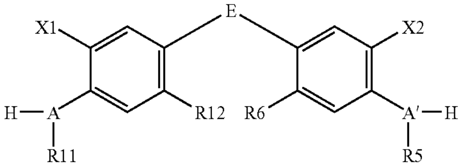

wherein R5, R6, R11, R12, A, A' and E each have the same meanings as defined in the formula 3, and, X1 and X2 are each independently a halogen atom;

[Formula 13]

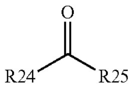

wherein

R24 and R25 are each independently an aryl or alkyl radical having 1 to 20 carbon atoms, and R24 and R25 may be bonded to each other;

[Formula 14]

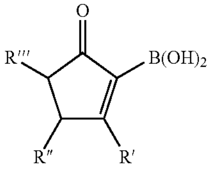

wherein

R', R'' and R''' are each independently a hydrogen atom; an alkyl radical having 1 to 20 carbon atoms; an aryl radical; a silyl radical; an alkenyl radical having 2 to 20 carbon atoms; an alkylaryl radical; an arylalkyl radical; or a metalloid radical of a Group 14 metal substituted with hydrocarbyl; and

[Formula 17]

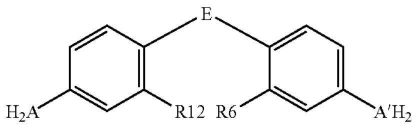

wherein R6, R12, A, A' and E each have the same meanings as defined in the formula 3; and $M(D(R26)_2)_4$ [Formula 16]

wherein M is a Group 4 transition metal, R26 is an aryl or alkyl radical having 1 to 20 carbon atoms, and D is a nitrogen or phosphorous atom.

* * * * *

UNITED STATES PATENT AND TRADEMARK OFFICE

CERTIFICATE OF CORRECTION

PATENT NO. : 7,678,933 B2
APPLICATION NO. : 12/087215
DATED : March 16, 2010
INVENTOR(S) : Choong-Hoon Lee et al.

It is certified that error appears in the above-identified patent and that said Letters Patent is hereby corrected as shown below:

On Title page of the patent, in the Abstract Item (57), line 17, "suzuki" should read --Suzuki--

Column 1, line 30, "1990's" should read --1990s--
Column 1, line 36, "yield" should read --yields--
Column 3, line 25, insert --compound-- between "The" and "(6)"
Column 5, line 66, insert --a-- between "is" and "tendency"
Column 6, line 32, "compound" should read --compounds--
Column 7, line 22, "is an alkyl radical" should read --are alkyl radicals--
Column 7, line 59, "suzuki" should read --Suzuki--
Column 7, line 65, insert --such-- between "configured" and "that"
Column 8, line 3, "keeps" should read --keep--
Column 8, line 11, "are" should read --is--
Column 15, line 29, insert --=-- between "X" and "a halogen"
Column 18, line 46, "suzuki" should read --Suzuki--
Column 18, line 48, insert --is-- between "as" and "conventionally"
Column 18, line 59, "each" should be deleted
Column 28, line 28, "was" should read --were--
Claim 1, Column 33, line 2, "ormula" should read --formula--
Claim 8, Column 36, line 49, "in dependently" should read --independently--
Claim 10, Column 37, line 44, "a organic" should read --an organic--
Claim 10, Column 38, line 51, the letter "N" should read --M--
Claim 11, Column 40, line 30, "a organic" should read --an organic--

Signed and Sealed this
Fifth Day of June, 2012

David J. Kappos

David J. Kappos
*Director of the United States Patent and Trademark Office*